US011666697B2

(12) United States Patent
D'Hoore et al.

(10) Patent No.: US 11,666,697 B2
(45) Date of Patent: Jun. 6, 2023

(54) METHODS FOR ENSURING RESUSPENSION OF PALIPERIDONE PALMITATE FORMULATIONS

(71) Applicant: Janssen Pharmaceutica NV, Beerse (BE)

(72) Inventors: Peter D'Hoore, Kasterlee (BE); Ignace Wallaert, Westmalle (BE); Jimmy Nguyen, Freemont, CA (US); Frank Meeussen, Westmalle (BE); Srihari Gopal, Belle Mead, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/534,837

(22) Filed: Nov. 24, 2021

(65) Prior Publication Data

US 2022/0168497 A1    Jun. 2, 2022

Related U.S. Application Data

(60) Provisional application No. 63/237,883, filed on Aug. 27, 2021, provisional application No. 63/119,305, filed on Nov. 30, 2020.

(51) Int. Cl.
| | | |
|---|---|---|
| *A61M 5/00* | (2006.01) | |
| *A61K 9/00* | (2006.01) | |
| *A61K 31/519* | (2006.01) | |
| *A61K 31/517* | (2006.01) | |
| *A61J 1/00* | (2006.01) | |

(52) U.S. Cl.
CPC ............ *A61M 5/002* (2013.01); *A61K 9/0019* (2013.01); *A61K 31/519* (2013.01); *A61J 1/00* (2013.01); *A61K 31/517* (2013.01); *A61M 2202/0007* (2013.01); *A61M 2205/21* (2013.01); *A61M 2209/06* (2013.01)

(58) Field of Classification Search
CPC ....... A61J 1/00; A61K 31/517; A61K 31/519; A61K 47/26; A61K 9/0019; A61K 9/10; A61M 2202/0007; A61M 2205/21; A61M 2209/06; A61M 5/002; A61P 25/18
See application file for complete search history.

(56) References Cited

U.S. PATENT DOCUMENTS

| | | |
|---|---|---|
| 5,254,556 A | 10/1993 | Janssen et al. |
| 6,077,843 A | 6/2000 | Francois et al. |
| 6,555,544 B2 | 4/2003 | Francois et al. |
| 9,439,906 B2 | 9/2016 | Vermeulen et al. |
| 10,143,693 B2 | 12/2018 | Gopal et al. |
| 11,304,951 B1 | 4/2022 | Gopal et al. |
| 11,324,751 B1 | 5/2022 | Gopal et al. |
| 11,439,647 B2 | 9/2022 | Milz et al. |
| 2022/0062557 A1 | 3/2022 | Wallaert et al. |

FOREIGN PATENT DOCUMENTS

| | | |
|---|---|---|
| EP | 3311374 B1 | 7/2020 |
| WO | 2016/199170 A2 | 12/2016 |

OTHER PUBLICATIONS

Gopal, S., et al., Practical guidance for dosing and switching from paliperidone palmitate 1 monthly to 3 monthly formulation in schizophrenia, Current Medical Research and Opinion, vol. 31, No. 11, Oct. 2, 2015, pp. 2043-2054.
Bydureon Bcise(Registered) (exenatide extended-release) injectable suspension, for subcutaneous use. Initial U.S. Approval: 2005, Prescribing information for Bydureon Bcise, revised Feb. 2020, 19 pages.
Clinical trial NCT01515423 entitled "A Randomized, Multicenter, Double Blind, Non-inferiority Study of Paliperidone Palmitate 3 Month and 1 Month Formulations for the Treatment of Subjects With Schizophrenia" (v40 Feb. 19, 2015).
Clinical Trial: History of Changes for Study: NCT03345342 A Study of Paliperidone Palmitate 6-Month Formulation, Nov. 2017 (v1).
Clinical Trials Identifier: NCT04072575, A Study of Paliperidone Palmitate 6-Month Formulation, Aug. 28, 2019.
Clinical Trials: History of Changes for Study: NCT04072575 A Study of Paliperidone Palmitate 6-Month Formulation, Aug. 27, 2019 (v1).
Clinical Trials: History of Changes for Study: NCT04072575, A Study of Paliperidone Palmitate 6-Month Formulation, Sep. 18, 2020 (v11).

(Continued)

*Primary Examiner* — Sarah Pihonak
(74) *Attorney, Agent, or Firm* — BakerHostetler

(57) ABSTRACT

Provided are methods for improving resuspendability of a paliperidone palmitate extended-release injectable suspension within a syringe, for reducing a force required for injection of a paliperidone palmitate extended-release injectable suspension, or for reducing the likelihood of incomplete injection of a paliperidone palmitate extended-release injectable suspension comprising maintaining the syringe in a desired orientation during shipping of the syringe that varies from the orientation of the syringe during pre-shipping storage. Also provided are populations of syringes that respectively contain paliperidone palmitate extended release injectable suspension, wherein each of the syringes have been shipped to a destination, and the syringes were each maintained in a desired orientation during shipping of the syringe that varies from the orientation of the syringe during pre-shipping storage. The present disclosure also provides pharmaceutical products comprising a paliperidone palmitate extended-release injectable suspension within a syringe for administration to a patient suffering from schizophrenia, wherein the syringe has undergone pre-shipping storage and has been shipped, and wherein the syringe has been maintained in an orientation during the shipping that varies from the orientation of the syringe during pre-shipping storage.

25 Claims, 5 Drawing Sheets

(56) References Cited

OTHER PUBLICATIONS

ClinicalTrials.Gov., "NCT01515423: Study of Paliperidone Palmitate 3 Month and 1 Month Formulations for the Treatment of Patients with Schizophrenia,", Mar. 11, 2014, (v.36).
EU Clinical Trials Register; EudraCT No. 2017-001941-28; 2018 (Year: 2018).
Invega Sustenna® (paliperidone palmitate) extended-release injectable suspension, for intramuscular use Initial U.S. Approval, Reference ID 3657038, Nov. 1, 2014, pp. 1-56.
Invega Sustenna® (paliperidone palmitate) extended-release injectable suspension, for intramuscular use Initial U.S. Approval: 2006.
Invega Trinza® (paliperidone palmitate) extended-release injectable suspension, for intramuscular use Initial U.S. Approval: 2006, pp. 16.
Invega Trinza® (paliperidone palmitate) extended-release injectable suspension, for intramuscular use Initial U.S. Approval: 2006, pp. 55.
Jain et al., An observational study of the effect of vibration on the caking of suspensions in oily vehicles, Int'l Journal of Pharmaceutics 514 (2016) 308-313.

METHODS FOR ENSURING RESUSPENSION OF PALIPERIDONE PALMITATE FORMULATIONS

CROSS-REFERENCE TO RELATED APPLICATIONS

The present application claims the benefit of priority to U.S. Provisional Application No. 63/237,883, filed Aug. 27, 2021, and U.S. Provisional Application No. 63/119,305, filed Nov. 30, 2020.

TECHNICAL FIELD

The present disclosure pertains to methods affecting the quality of administration of a pharmaceutical suspension.

BACKGROUND

Antipsychotic medications are the mainstay in the treatment of schizophrenia, schizoaffective disorder, and schizophreniform disorders. Antipsychotics were first introduced in the mid-1950s. These typical or first generational drugs are usually effective in controlling the positive symptoms of schizophrenia but are less effective in moderating the negative symptoms or the cognitive impairment associated with the disease. Atypical antipsychotics or second-generation drugs, typified by risperidone and olanzapine, were developed in the 1990s, and are generally characterized by effectiveness against both the positive and negative symptoms associated with schizophrenia.

Paliperidone palmitate is the palmitate ester of paliperidone (9-hydroxy-risperidone), a monoaminergic antagonist that exhibits the characteristic dopamine type 2 ($D_2$) and serotonin (5-hydroxytryptamine type 2A) antagonism of the second generation, atypical antipsychotic drugs. Paliperidone (9-OH risperidone) is the major active metabolite of risperidone. Extended release (ER) osmotic controlled release oral delivery (OROS) paliperidone, as a tablet formulation, is marketed in the United States (U.S.) for the treatment of schizophrenia and maintenance of effect.

Paliperidone palmitate has been developed as a long-acting, intramuscular (i.m.), injectable aqueous nanosuspension for the treatment of schizophrenia and other related diseases that are normally treated with antipsychotic medications. Because of extreme low water solubility, paliperidone esters such as paliperidone palmitate dissolve slowly after an intramuscular injection before being hydrolyzed to paliperidone and made available in the systemic circulation.

Once-monthly paliperidone palmitate injection has been developed to provide sustained plasma concentrations of paliperidone, which may greatly enhance compliance with dosing. Paliperidone palmitate formulated as an aqueous nanosuspension is described in U.S. Pat. Nos. 6,077,843 and 6,555,544, each of which is incorporated herein by reference. In addition, dosing regimens of paliperidone palmitate for treating patients is disclosed in U.S. Pat. Nos. 9,439,906 and 10,143,693, each of which is incorporated herein by reference.

Paliperidone is currently available for therapeutic use in three formulations: an oral extended-release formulation (INVEGA® Extended Release [ER] tablets; also termed INVEGA® prolonged-release [PR] tablets), and two long-acting injectable (LAI) formulations (paliperidone palmitate 1-month injection [INVEGA SUSTENNA® or XEPLION®] and paliperidone palmitate 3-month injection [INVEGA TRINZA® or TREVICTA®]). Another paliperidone palmitate product intended for administration once every 6 months (paliperidone palmitate 6-month injection) has been approved in the United States [INVEGA HAFYERA™] and Europe [BYANNLI®], with a view towards further improving adherence and convenience.

Paliperidone palmitate suspension formulations are typically highly concentrated products. As a result, an important consideration is to ensure complete suspension/resuspension of the product before administration. To minimize the chances of incomplete administration, it is necessary for a health care professional to conduct the administration, and to follow specific guidelines in preparation for and during the administration. For example, the INVEGA TRINZA® label specifies that the syringe containing the formulation should be shaken vigorously for at least 15 seconds prior to administration in order to ensure a homogeneous suspension (corresponding to instructions for use, IFU). It is also necessary to perform the injection slowly, for example, over a period of 20-30 seconds. It is also recommended that shaking is performed while the syringe is in the tip-up position. The label for INVEGA HAFYERA™ specifies that the syringe containing the formulation should be shaken (with the syringe tip cap pointing up) very fast for at least 15 seconds, followed by a brief rest, and then shaken again for 15 seconds.

It is possible that there may be some instances of deviation from the resuspension protocols due to human error that could lead to insufficient resuspension and, as a result, incomplete administration of paliperidone palmitate suspension. A need exists for additional strategies for ensuring that the required resuspension of paliperidone palmitate occurs.

SUMMARY

Provided herein are methods for improving resuspendability of a paliperidone palmitate extended-release injectable suspension within a syringe comprising maintaining the syringe in a substantially horizontal orientation during shipping of the syringe. Also provided herein are methods for improving resuspendability of a paliperidone palmitate extended-release injectable suspension within a syringe comprising maintaining the syringe in an orientation during shipping that varies from the orientation of the syringe during pre-shipping storage, such as in a substantially horizontal orientation during shipping of the syringe when the orientation during pre-shipping storage was not substantially horizontal.

Also disclosed are methods for reducing a force required for injection of a paliperidone palmitate extended-release injectable suspension from a syringe comprising maintaining the syringe in a substantially horizontal orientation during shipping of the syringe. Also disclosed are methods for reducing a force required for injection of a paliperidone palmitate extended-release injectable suspension from a syringe comprising maintaining the syringe in an orientation during shipping that varies from the orientation of the syringe during pre-shipping storage, such as in a substantially horizontal orientation during shipping of the syringe when the orientation during pre-shipping storage was not substantially horizontal.

The present disclosure also pertains to methods for reducing the likelihood of incomplete injection of a paliperidone palmitate extended-release injectable suspension from a syringe comprising maintaining the syringe in a substantially horizontal orientation during shipping of the syringe. The present disclosure also pertains to methods for reducing the likelihood of incomplete injection of a paliperidone palmitate extended-release injectable suspension from a syringe comprising maintaining the syringe in an orientation during shipping that varies from the orientation of the syringe during pre-shipping storage, such as in a substantially horizontal orientation during shipping of the syringe when the orientation during pre-shipping storage was not substantially horizontal.

Also provided are methods for improving resuspendability of a paliperidone palmitate extended-release injectable suspension within a syringe comprising maintaining the syringe in a substantially horizontal orientation during storage of the syringe. Also provided are methods for improving resuspendability of a paliperidone palmitate extended-release injectable suspension within a syringe comprising maintaining the syringe in an orientation during shipping that varies from the orientation of the syringe during pre-shipping storage, such as in a substantially horizontal orientation during storage of the syringe when the orientation during pre-shipping storage was not substantially horizontal.

Also disclosed are populations of syringes that respectively contain paliperidone palmitate extended release injectable suspension, wherein each of the syringes have been shipped to a destination, and the syringes were each maintained in a substantially horizontal orientation during shipping of the syringe. Also disclosed are populations of syringes that respectively contain paliperidone palmitate extended release injectable suspension, wherein each of the syringes have been shipped to a destination, and the syringes were each maintained in an orientation during shipping that varies from the orientation of the syringes during pre-shipping storage, such as in a substantially horizontal orientation during shipping of the syringes when the orientation during pre-shipping storage was not substantially horizontal.

The present disclosure also provides pharmaceutical products that comprise a paliperidone palmitate extended-release injectable suspension within a syringe for administration to a patient suffering from schizophrenia, wherein the syringe has undergone pre-shipping storage and has been shipped, and wherein the syringe has been maintained in an orientation during the shipping that varies from the orientation of the syringe during pre-shipping storage.

Also disclosed are methods of treating schizophrenia comprising administering to a patient suffering from schizophrenia a paliperidone palmitate extended-release injectable suspension from a syringe, wherein the syringe has undergone pre-shipping storage and has been shipped, and wherein the syringe was maintained in an orientation during the shipping that varied from the orientation of the syringe during pre-shipping storage. Also disclosed are paliperidone palmitate extended-release injectable suspensions for use in methods of treating schizophrenia, wherein these methods comprise administering to a patient suffering from schizophrenia the paliperidone palmitate extended-release injectable suspension from a syringe, wherein the syringe has undergone pre-shipping storage and has been shipped, and wherein the syringe was maintained in an orientation during the shipping that varied from the orientation of the syringe during pre-shipping storage. Also disclosed is the use of a paliperidone palmitate extended-release injectable suspension in the manufacture of a medicament for treating schizophrenia, wherein the paliperidone palmitate extended-release injectable suspension is prepared for administration from a syringe, wherein the syringe has undergone pre-shipping storage and has been shipped, and wherein the syringe was maintained in an orientation during the shipping that varied from the orientation of the syringe during pre-shipping storage.

In embodiments of the present disclosure, the paliperidone palmitate extended-release injectable suspension is selected from the group consisting of PP3M and PP6M. In one embodiment, the paliperidone palmitate extended-release injectable suspension is PP3M. In one embodiment, the paliperidone palmitate extended-release injectable suspension is PP6M.

DETAILED DESCRIPTION OF ILLUSTRATIVE EMBODIMENTS

Figure 1A:
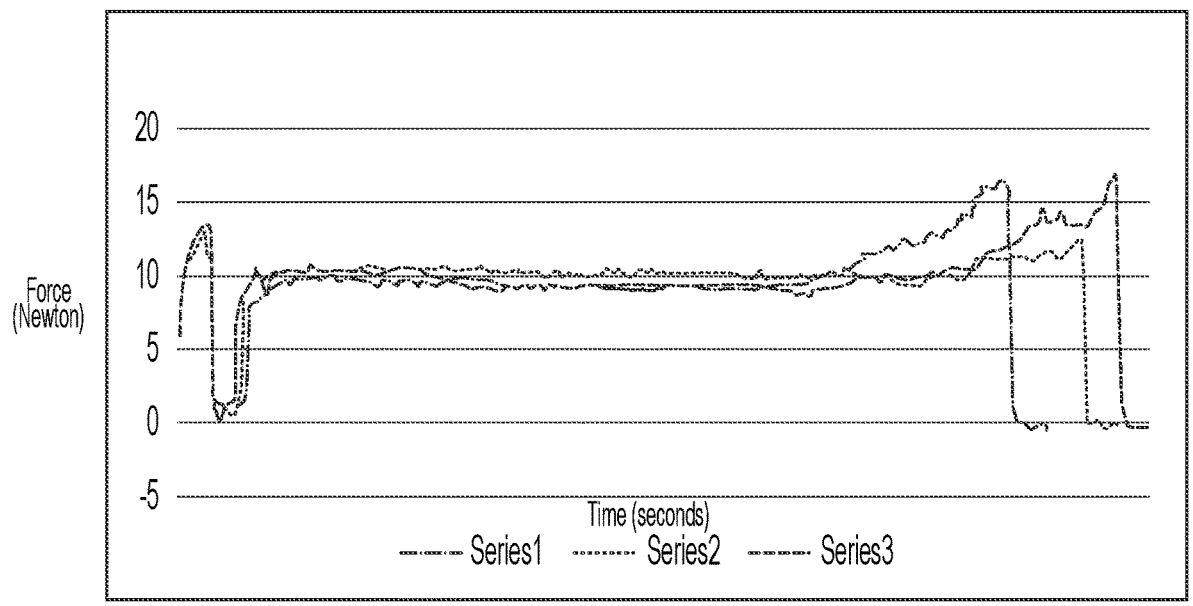
FIGS. 1A-1F depict force injection profiles for process performance qualification (PPQ) batches of PP6M that were respectively stored in one of five different spatial orientations.
Figure 1B:
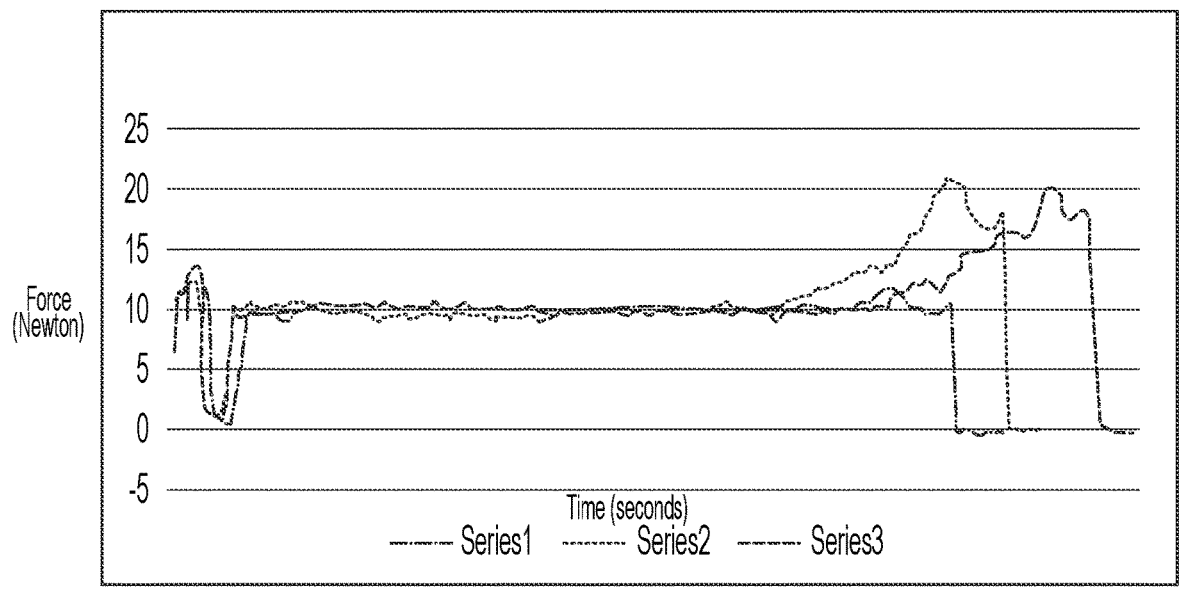
Figure 1C:
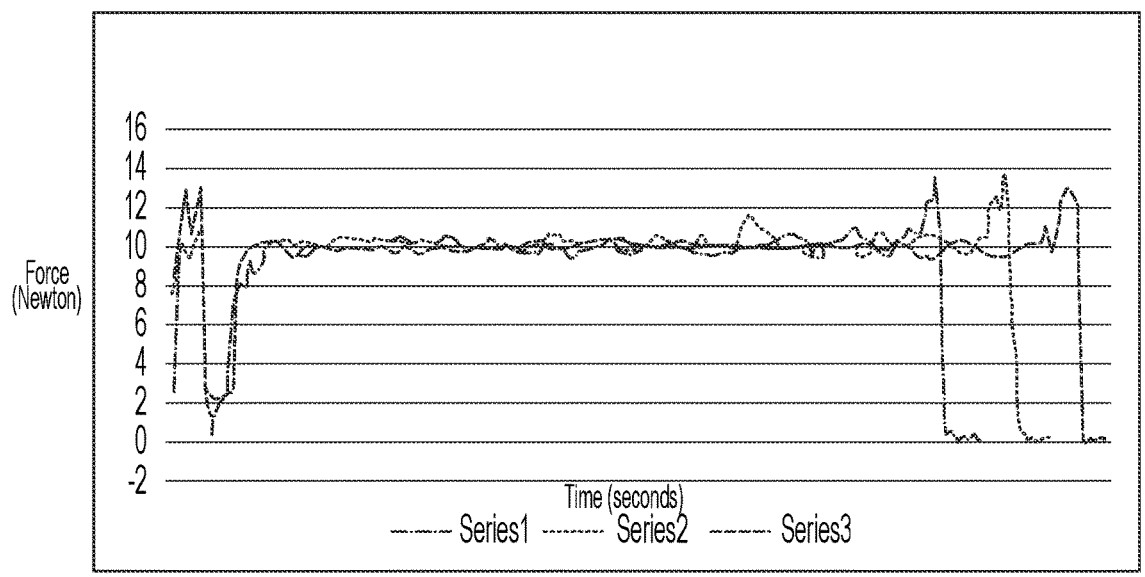
Figure 1D:
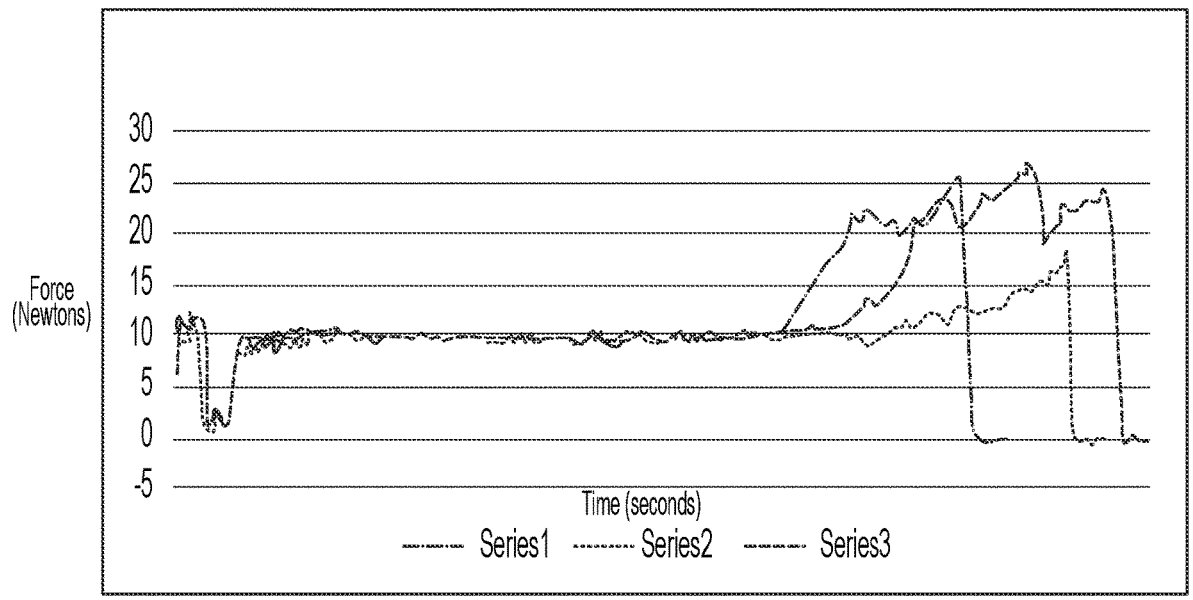
Figure 1E:
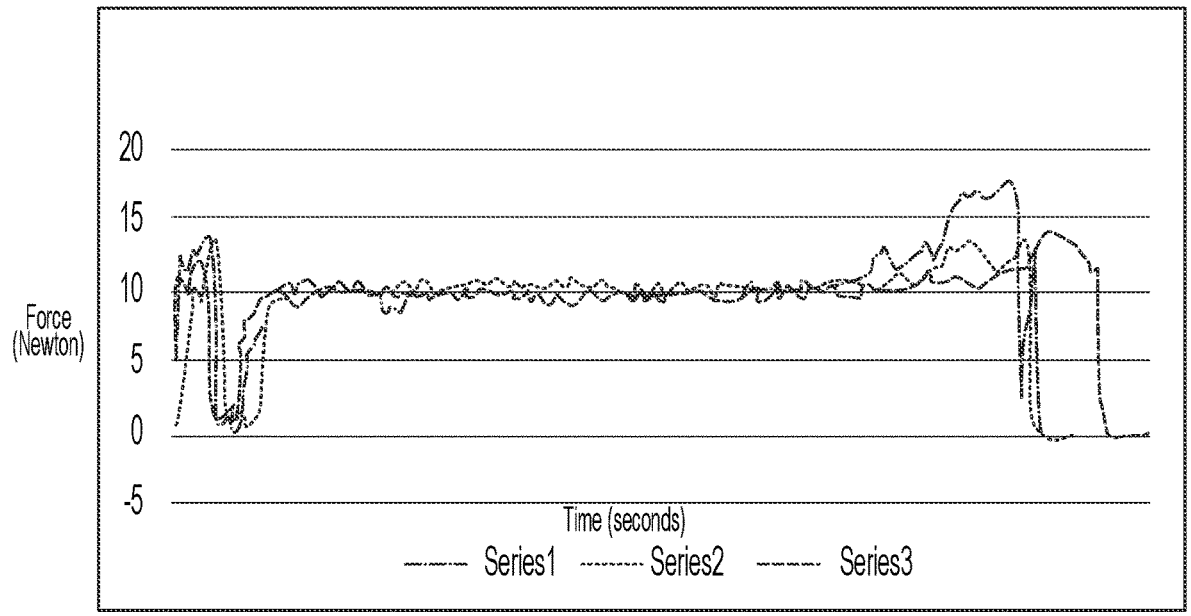
Figure 1F:
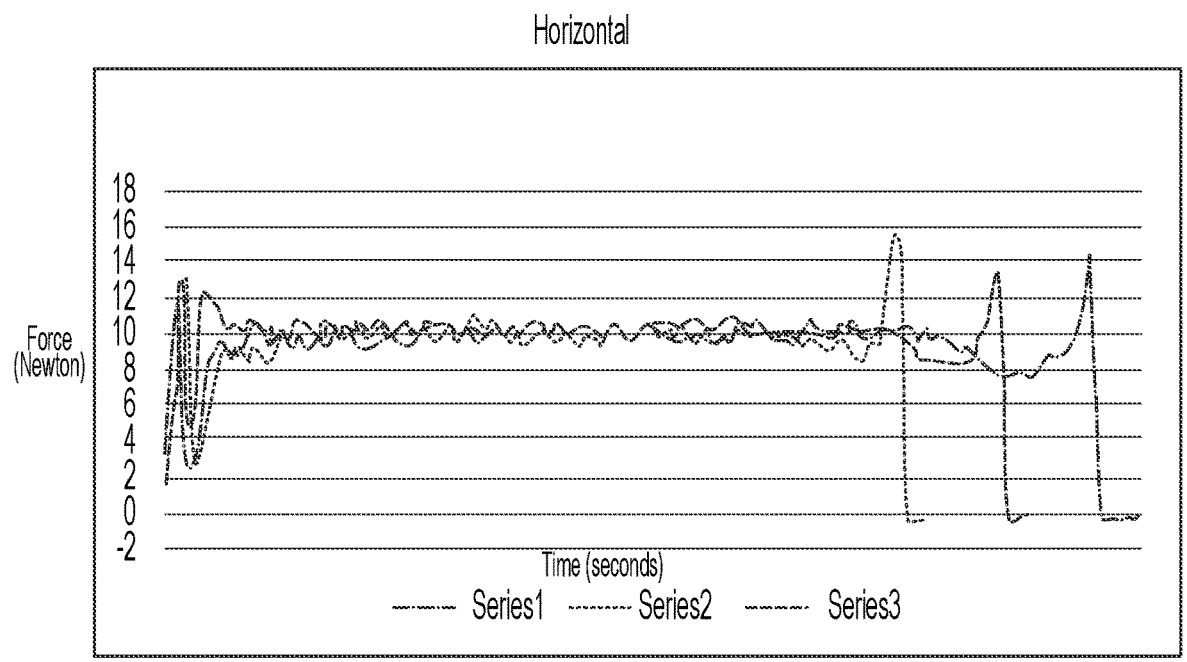

The presently disclosed inventive subject matter may be understood more readily by reference to the following detailed description taken in connection with the accompanying examples, which form a part of this disclosure. It is to be understood that these inventions are not limited to the specific formulations, methods, or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a formulation" is a reference to one or more of such formulation and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. In some embodiments, "about X" (where X is a numerical value) refers to ±10% of the recited value, inclusive. For example, the phrase "about 8" can refer to a value of 7.2 to 8.8, inclusive. This value may include "exactly 8". Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

It should be understood that references herein to methods of treatment (e.g., methods of treating schizophrenia) using one or more compounds or formulations thereof (e.g., paliperidone palmitate extended release injectable suspension) should also be interpreted as references to:

one or more compounds or formulations thereof (e.g. paliperidone palmitate extended-release injectable suspension) for use in methods of treating, e.g., schizophrenia; and/or the use of one or more compounds of formulations thereof (e.g., a paliperidone palmitate extended-release injectable suspension) in the manufacture of a medicament for treating, e.g., schizophrenia.

As described above, resuspension protocols exist in order to ensure complete administration of paliperidone palmitate injectable suspension. Although prescribed paliperidone palmitate formulations include clear label instructions concerning the correct procedure for preparing the formulations for administration and for the mode in which the injection itself should be performed, it is possible that health care personnel who are charged with following the specified procedures may not do so in a manner that ensures adequate resuspension of paliperidone palmitate and thereby delivery of the prescribed dosage to the patient in need.

The present inventors have surprisingly discovered that varying the orientation of the syringes that contain the paliperidone palmitate suspension during the shipping process relative to the orientation of the syringes during a pre-shipping storage period influences the resuspendability of the drug product in preparation for administration. In particular, it has been found that maintaining the syringes in an orientation during shipping that varies from the orientation of the syringe during pre-shipping storage, such as in a substantially horizontal orientation during shipping, for example, as opposed to the traditional tip-down orientation when the syringes were also stored prior to shipping in a tip-down orientation, improves the resuspendability of the paliperidone palmitate, and thereby improves the likelihood that complete administration of the prescribed dosage occurs. Therefore, the present discovery has the effect of mitigating human error or other causes of deviation from the prescribed resuspension protocol (e.g., governing the type and duration of shaking) that is intended to ensure adequate resuspension of the paliperidone palmitate. As a result of the improvement in the resuspension of drug, certain benefits accrue, such as the reduction in the amount of force required for administration, and, as a general matter, the chances of incomplete administration are reduced. This can also improve resuspension by reducing the force of the shaking that is required for resuspension. The fact that the chances of incomplete administration are reduced means, in turn, that the risk of a patient receiving a lower-than-intended dose of paliperidone palmitate is also reduced. This means that in instances of deviation from the prescribed resuspension protocol, a patient suffering from schizophrenia who is administered paliperidone palmitate extended-release injectable suspension from a syringe which has, for example, been maintained in an orientation during shipping that varies from the orientation of the syringe during pre-shipping storage, such as in a substantially horizontal orientation during shipping, is less likely to receive a lower-than-intended dose than a patient who has been administered paliperidone palmitate extended-release injectable suspension from a syringe which has, for example, been maintained in the traditional tip-down orientation during shipping. Thus, the administration of a paliperidone palmitate extended-release injectable suspension from a syringe which has, for example, been maintained in an orientation during shipping that varies from the orientation of the syringe during pre-shipping storage, such as in a substantially horizontal orientation during shipping, represents an important contribution to the field of schizophrenia therapy.

Accordingly, provided herein are methods for improving resuspendability of a paliperidone palmitate extended-release injectable suspension within a syringe comprising maintaining the syringe in a substantially horizontal orientation during shipping of the syringe. The present disclosure also embraces methods for reducing the likelihood of incomplete injection of a paliperidone palmitate extended release injectable suspension from a syringe, comprising maintaining the syringe in a substantially horizontal orientation during shipping of the syringe. Also provided herein are methods for improving resuspendability of a paliperidone palmitate extended-release injectable suspension within a syringe comprising maintaining the syringe in an orientation during shipping that varies from the orientation of the syringe during pre-shipping storage, such as in a substantially horizontal orientation during shipping of the syringe when the orientation during pre-shipping storage was not substantially horizontal. The present disclosure also embraces methods for reducing the likelihood of incomplete injection of a paliperidone palmitate extended release injectable suspension from a syringe, comprising maintaining the syringe in an orientation during shipping that varies from the orientation of the syringe during pre-shipping storage, such as in a substantially horizontal orientation during shipping of the syringe when the orientation during pre-shipping storage was not substantially horizontal.

In embodiments of the present disclosure, the paliperidone palmitate extended-release injectable suspension is selected from the group consisting of PP3M and PP6M. In one embodiment, the paliperidone palmitate extended-release injectable suspension is PP3M. In one embodiment, the paliperidone palmitate extended-release injectable suspension is PP6M.

Paliperidone esters are antipsychotic agents belonging to the chemical class of benzisoxazole derivatives, which contains a racemic mixture of (+)- and (−)-paliperidone, which are described in U.S. Pat. No. 5,254,556 (incorporated herein by reference). The chemical name for paliperidone palmitate is (±)-3-[2[4-(6-fluoro-1,2-benzisoxazol-3-yl)-1-piperidinyl]ethyl]-6,7,8,9-tetrahydro-2-methyl-4-oxo-4H-pyrido[1,2-c]pyrimidin-9-yl hexadecanoate. The structural formula is:

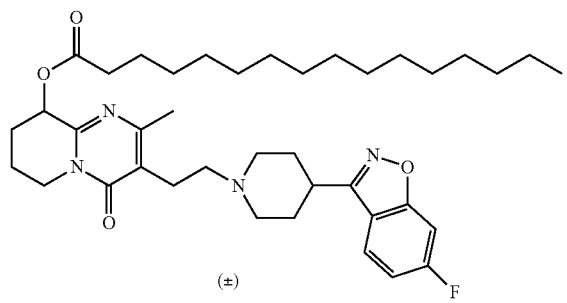 [SMILES: CCCCCCCCCCCCCCCC(=O)OC1CCCn2c1nc(C)c(CCN1CCC(c3noc4cc(F)ccc34)CC1)c2=O]

Paliperidone esters may be formulated with pharmaceutical excipients into injectable dosage forms as described in U.S. Pat. Nos. 5,254,556 and 6,077,843 both of which are incorporated herein by reference. Injectable formulations may be formulated in aqueous carriers.

The paliperidone palmitate extended-release injectable suspension may be, for example, a commercially available formulation that is intended for administration to a subject once every three months, once every six months, or some other interval.

Commercially available formulations that are for administration once every three months include INVEGA TRINZA® or TREVICTA®. See also U.S. Pat. No. 10,143,693 incorporated herein by reference. In the present disclosure, "PP3M" refers to a paliperidone palmitate extended-release injectable suspension or other type of formulation having an amount of paliperidone palmitate suitable for a dosing interval of about three-months. For example, "PP3M" can refer to a paliperidone palmitate extended-release injectable suspension having a dosing interval of about three-months.

Commercially available formulations that are for administration once every six months include INVEGA HAFYERA™ in the United States. A formulation for administration once every six months has received marketing authorization in Europe under the trade name BYANNLI®. In the present disclosure, "PP6M" refers to a paliperidone palmitate extended-release injectable suspension or other type of formulation having an amount of paliperidone palmitate suitable for a dosing interval of about six-months. For example, "PP6M" can refer to a paliperidone palmitate extended-release injectable suspension having a dosing interval of about six-months. PP6M will typically be provided with a dose in the range of from about 1000 mg to about 1600 mg of paliperidone palmitate to provide a sustained therapeutic concentration of paliperidone over the six-month dosing interval. Preferably, the PP6M will be provided in dose strengths of about 1092 mg or about 1560 mg paliperidone palmitate. The drug product hydrolyzes to the active moiety, paliperidone, resulting in dose strengths of about 700 mg eq. or 1000 mg eq. of paliperidone, respectively.

PP6M is preferably provided in a prefilled syringe (cyclic-olefin-copolymer) prefilled with either 700 mg eq. (3.5 mL) or 1000 mg eq. (5.0 mL) paliperidone (as 1092 mg or 1560 mg paliperidone palmitate, respectively) with a plunger stopper, a plunger rod, and tip cap (bromobutyl rubber), a backstop, and a needle, preferably a thin walled 20 gauge (G), 1.5-inch safety needle.

PP3M will typically be provided with a dose in the range of from about 270 mg to about 825 mg of paliperidone palmitate to provide a sustained therapeutic concentration of paliperidone over the three-month dosing interval. Preferably, the PP3M will be provided in dose strengths of about 273, 410, 546, or 819 mg paliperidone palmitate. The drug product hydrolyzes to the active moiety, paliperidone, resulting in dose strengths of about 175, 263, 350, or 525 mg eq. of paliperidone, respectively.

PP3M is preferably provided in a prefilled syringe (cyclic-olefin-copolymer) prefilled with about 175 mg eq. to about 525 mg eq. with a plunger stopper, a plunger rod, and tip cap (bromobutyl rubber), a backstop, and a needle, preferably a thin walled 20 gauge (G), 1.5-inch safety needle, or a thin walled 22 gauge (G), 1-inch safety needle.

In certain embodiments, PP3M and PP6M can have the same formulation, and differ in terms of the total volume of the suspension formulation that is housed within respective syringes. The paliperidone palmitate suspension that is used pursuant to the present methods may contain, in absolute amounts, about 250 to about 1600 mg of paliperidone palmitate. The amount of paliperidone palmitate in the suspension may be, for example, 273, 410, 546, or 819 mg. In certain embodiments, the amount of paliperidone palmitate in the suspension may be 1092 or 1560 mg.

In certain embodiments, a 3-month (PP3M) formulation has average particle sizes of less than about 20 µm to about 1 µm. In other embodiments, the particles have an average particle size (d50) of from about 5 µm to about 15 µm; from about 3 µm to about 10 µm; or from about 5 µm to about 9 µm. The d90 may be about 50 µm; from about 10 µm to about 30 µm; or from about 10 µm to about 20 µm. The d10 may be from about 1 µm to about 10 µm, or about 1 µm to about 5 µm.

In certain embodiments, a 6-month (PP6M) formulation has an average particle size of less than about 30 µm to about 1 µm; or about 20 µm to about 1 µm. In other embodiments, the particles have an average particle size (d50) of from about 3 µm to about 25 µm; from about 5 µm to about 15 µm; from about 3 µm to about 10 µm; or from about 5 µm to about 9 µm. The d90 may be 60 µm; or about 50 µm; from about 10 µm to about 30 µm; or from about 10 µm to about 20 µm. The d10 may be from about 1 µm to about 15 µm; from about 1 µm to about 10 µm; or about 1 µm to about 5 µm.

As used herein, d10: the portion of particles with diameters smaller than this value is 10%; d50: the portion of particles with diameters smaller than this value are 50%; d90: the portion of particles with diameters smaller than this value is 90%; when measured by art-known conventional techniques, such as sedimentation field flow fractionation, photon correlation spectroscopy or disk centrifugation.

Suitable aqueous nanoparticle formulations are described in U.S. Pat. No. 6,555,544 which is incorporated herein by reference. In some embodiments, the formulation comprises micro particles, a surfactant, a suspending agent, and optionally one or more additional ingredients selected from the group consisting of preservatives, buffers and an isotonizing agent.

Useful surface modifiers for paliperidone palmitate formulations are believed to include those that physically adhere to the surface of the active agent but do not chemically bond thereto. Suitable surface modifiers can be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available TWEENs™, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminate silicate, triethanolamine, polyvinyl alcohol (PVA), poloxamers, tyloxapol and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone; tyloxapol; poloxamers, such as PLURONIC™ F68, F108 and F127 which are block copolymers of ethylene oxide and propylene oxide available from BASF; poloxamines, such as TETRONIC™ 908 (T908) which is a tetrafunctional block copolymer derived from sequential addition of ethylene oxide and propylene oxide to ethylenediamine available from BASF; dextran; lecithin; Aerosol OT™ (AOT) which is a dioctyl ester of sodium sulfosuccinic acid available from Cytec Industries; DUPONOL™ P which is a sodium lauryl sulfate available from DuPont; TRITON™ X-200 which is an alkyl aryl polyether sulfonate available from Rohm and Haas; TWEEN™ 20, 40, 60 and 80 which are polyoxyethylene sorbitan fatty acid esters available from ICI Specialty Chemicals; SPAN™ 20, 40, 60 and 80 which are sorbitan esters of fatty acids; ARLACEL™ 20, 40, 60 and 80 which are sorbitan esters of fatty acids available from Hercules, Inc.; CARBOWAX™ 3550 and 934 which are polyethylene glycols available from Union Carbide; CRODESTA™ F110 which is a mixture of sucrose stearate and sucrose distearate available from Croda Inc.; CRODESTA™ SL-40 which is available from Croda, Inc.; hexyldecyl trimethyl ammonium chloride (CTAC); bovine serum albumin, and SA90HCO which has the formula as follows: $C_{18}H_{17}CH_2(CON(CH_3)CH_2(CHOH)_4CH_2OH)_2$. The surface modifiers which have been found to be particularly useful include tyloxapol and a poloxamer, preferably, Pluronic™ F108 and Pluronic™ F68.

Pluronic™ F108 corresponds to poloxamer 338 and is the polyoxyethylene, polyoxypropylene block copolymer that conforms generally to the formula $HO[CH_2CH_2O]_x[CH(CH_3)CH_2O]_y[CH_2CH_2O]_zH$ in which the average values of x, y and z are respectively 128, 54 and 128. Other commercial names of poloxamer 338 are Hodag NONIONIC™ 1108-F available from Hodag, and SYNPERONIC™ PE/F108 available from ICI Americas.

The optimal relative amount of paliperidone palmitate and the surface modifier depends on various parameters. The optimal amount of the surface modifier can depend, for example, upon the particular surface modifier selected, the critical micelle concentration of the surface modifier if it forms micelles, the surface area of the antipsychotic agent, etc. The specific surface modifier preferably is present in an amount of about 0.1 to about 1 mg per square meter surface area of the paliperidone palmitate. It is preferred in the case of paliperidone palmitate (9-hydroxyrisperidone palmitate) to use PLURONIC™ F108 as a surface modifier, a relative amount (w/w) of both ingredients of approximately 6:1 is preferred.

The particles of a paliperidone palmitate suspension can be prepared by a method comprising the steps of dispersing paliperidone palmitate in a liquid dispersion medium and applying mechanical means in the presence of grinding media to reduce the particle size of the antipsychotic agent to an effective average particle size. The particles can be reduced in size in the presence of a surface modifier. Alternatively, the particles can be contacted with a surface modifier after attrition.

A general procedure for preparing the particles of a paliperidone palmitate suspension may include (a) obtaining paliperidone palmitate; (b) adding the paliperidone palmitate to a liquid medium to form a premix; and (c) subjecting the premix to mechanical means in the presence of a grinding medium to reduce the effective average particle size.

The paliperidone palmitate may be prepared using techniques known in the art. It is preferred that the particle size of the paliperidone palmitate be less than about 100 μm as determined by sieve analysis. If the particle size of the paliperidone palmitate is greater than about 100 μm, then it is preferred that the particles of paliperidone palmitate be reduced in size to less than 100 μm.

The paliperidone palmitate can then be added to a liquid medium in which it is essentially insoluble to form a premix. The concentration of paliperidone palmitate in the liquid medium (weight by weight percentage) can vary widely and depends on the selected antipsychotic agent, the selected surface modifier and other factors. Suitable concentrations of paliperidone palmitate in compositions vary from about 0.1% to about 60%, preferably is from about 0.5% to about 30%, and more preferably, is approximately 7% (w/v). For PP3M, it is preferred to use a concentration of about 200 mg eq. of paliperidone per mL or about 312 mg of paliperidone palmitate per mL. For PP6M, it is preferred to use a concentration of about 200 mg eq. of paliperidone per mL or about 312 mg of paliperidone palmitate per mL.

Another exemplary procedure involves the addition of a surface modifier to the premix prior to its subjection to mechanical means to reduce the effective average particle size. The concentration of the surface modifier (weight by weight percentage) can vary from about 0.1% to about 90%, preferably from about 0.5% to about 80%, and more preferably is approximately 7% (w/v).

The premix can be used directly by subjecting it to mechanical means to reduce the effective average particle size in the dispersion to the desired particle size. It is preferred that the premix be used directly when a ball mill is used for attrition. Alternatively, the antipsychotic agent and, optionally, the surface modifier, can be dispersed in the liquid medium using suitable agitation such as, for example, a roller mill or a Cowles type mixer, until a homogeneous dispersion is achieved.

The mechanical means applied to reduce the effective average particle size of the antipsychotic conveniently can take the form of a dispersion mill. Suitable dispersion mills include a ball mill, an attritor mill, a vibratory mill, a planetary mill, media mills—such as a sand mill and a bead mill. A media mill is preferred due to the relatively shorter milling time required to provide the desired reduction in particle size. For media milling, in some embodiments, the apparent viscosity of the premix preferably is anywhere between about 0.1 Pa·s and about 1 Pa·s. In some embodiments, for ball milling, the apparent viscosity of the premix preferably is anywhere between about 1 mPa·s and about 100 mPa·s.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of the material for the grinding media is believed not to be critical. However, about 95% ZrO stabilized with magnesia, zirconium silicate, and glass grinding media provide particles which are acceptable for the preparation of pharmaceutical compositions. Further, other media, such as polymeric beads, stainless steel, titania, alumina and about 95% ZrO stabilized with yttrium, are useful. Preferred grinding media have a density greater than about 2.5 g/cm$^3$ and include about 95% ZrO stabilized with magnesia and polymeric beads.

The attrition time can vary widely and depends primarily upon the particular mechanical means and processing conditions selected. For rolling mills, processing times of up to two days or longer may be required for smaller size particles.

The particles should be reduced in size at a temperature which does not significantly degrade the antipsychotic agent. Processing temperatures of less than about 30° C. to about 40° C. are ordinarily preferred. If desired, the processing equipment may be cooled with conventional cooling equipment. The method is conveniently carried out under conditions of ambient temperature and at processing pressures which are safe and effective for the milling process.

The surface modifier, if it was not present in the premix, is typically added to the dispersion after attrition in an amount, for example, as described for the premix above. Thereafter, the dispersion can be mixed by, for example, shaking vigorously. Optionally, the dispersion can be subjected to a sonication step using, for example, an ultrasonic power supply.

Aqueous compositions may further comprise a suspending agent and a buffer, and optionally one or more of a preservative and an isotonizing agent. Particular ingredients may function as two or more of these agents simultaneously, e.g. behave like a preservative and a buffer, or behave like a buffer and an isotonizing agent.

Suitable suspending agents (also referred to as physical stabilizers) for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxy-propylene ethers. Preferably sodium carboxymethyl cellulose is used in a concentration of about 0.5 to about 2%, most preferably about 1% (w/v).

Suitable wetting agents preferred from the listed surfactant for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of about 0.5% to about 3%, more preferably about 0.5% to about 2%, most preferably about 1.1% (w/v).

Suitable buffering agents are salts of weak acids and should be used in amount sufficient to render the dispersion from about pH 6.0 to basic. Preferably, the pH is in a range of from about 6.0 to about 9.0; or in the range of from about 6.0 to about 8.0; or about 6.5 to about 7.5. For example, the pH is in the range of about 6.0 to about 6.5; or from about 6.5 to about 7.0; or from about 7.0 to about 7.5; or from about 7.5 to about 8.0; or from about 8.0 to about 8.5; or from about 8.5 to about 9.0. Particularly preferred is the use of a mixture of disodium hydrogen phosphate (anhydrous) (typically about 0.9% (w/v)) and sodium dihydrogen phosphate monohydrate (typically about 0.6% (w/v)). This buffer also renders the dispersion isotonic and, in addition, less prone to flocculation of the ester suspended therein.

Preservatives can include antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-gamma-piccolinium chloride, phenylmercuric acetate and thimerosal. In particular, it is benzyl alcohol which can be used in a concentration up to about 2% (w/v), preferably up to about 1.5% (w/v).

Isotonizing agents are, for example, sodium chloride, dextrose, mannitol, sorbitol, lactose, sodium sulfate. The suspensions conveniently comprise from about 0% to about 10% (w/v) isotonizing agent. Mannitol may be used in a concentration from about 0% to about 7% more preferably, however, from about 1% to about 3% (w/v), especially from about 1.5% to about 2% (w/v) of one or more electrolytes are used to render the suspension isotonic, apparently because ions help to prevent flocculation of the suspended ester. In particular, electrolytes of the buffer serve as isotonizing agent.

A particularly desirable feature for an injectable formulation relates to the ease with which it can be administered. In particular such an injection should be feasible using a needle as fine as possible in a span of time which is as short as possible. This can be accomplished with the aqueous suspensions of the present invention by maintaining certain viscosities that can be easily taken up in a syringe (e.g., from a vial), and injected through a fine needle. For example, in some embodiments the viscosity is below about 75 mPa·s, or below about 60 mPa·s at room temperature. For PP3M, a 22G, 1½ inch needle, or a 22G, 1 inch needle is typically used. For PP6M, a 20G, 1½ inch needle is typically used.

Ideally, aqueous suspensions for use in accordance with the present methods include as much prodrug as can be tolerated so as to keep the injected volume to a minimum, and as little of the other ingredients as possible.

In particular for PP3M or PP6M, the composition may comprise, or consist essentially of, (a) from about 200 to about 500 mg/mL of prodrug; (b) from about 2 to about 25 mg/mL of wetting agent; (c) from about 2.5 to about 50 mg/mL of one or more buffering agents; (d) from about 25 to about 150 mg/mL of a suspending agent; (e) optionally up to about 2% (w/v) preservatives; and (f) water q.s. ad 100%. Typically, the PP3M or PP6M composition has a pH of from about 6.0 to about 8.0, preferably about a pH of from 6.5 to about 7.5.

In other embodiments, for PP3M or PP6M, the composition may comprise or consist essentially of, (a) from about 250 to about 400 mg/mL of prodrug; (b) from about 5 to about 20 mg/mL of wetting agent; (c) from about 5 to about 25 mg/mL of one or more buffering agents; (d) from about 50 to about 100 mg/mL of a suspending agent; (e) optionally up to about 2% (w/v) preservatives; and (f) water q.s. ad 100%.

In other embodiments, for PP3M or PP6M, the composition may comprise or consist essentially of, (a) from about 280 to about 350 mg/mL of prodrug; (b) from about 8 to about 12 mg/mL of wetting agent; (c) from about 5 to about 15 mg/mL of one or more buffering agents; (d) from about 65 to about 85 mg/mL of a suspending agent; (e) optionally up to about 2% (w/v) preservatives; and (f) water q.s. ad 100%.

The active ingredient in PP3M or PP6M comprises paliperidone palmitate (about 312 mg/mL). In certain preferred embodiments, the inactive ingredients in PP3M or PP6M will be polysorbate 20 (about 10 mg/mL), polyethylene glycol 4000 (about 75 mg/mL), citric acid monohydrate (about 7.5 mg/mL), sodium dihydrogen phosphate monohydrate (about 6 mg/mL), sodium hydroxide (about 5.4 mg/mL) and water for injection. An exemplified PP3M is disclosed in Example 1. An exemplified PP6M is disclosed in Example 2.

The present methods include maintaining a syringe containing a paliperidone palmitate extended-release injectable suspension in a substantially horizontal orientation during shipping of the syringe. The present methods also include maintaining a syringe containing a paliperidone palmitate extended-release injectable suspension in an orientation during shipping that varies from the orientation of the syringe during pre-shipping storage, such as in a substantially horizontal orientation during shipping of the syringe when the orientation during pre-shipping storage was not substantially horizontal.

Regardless of the particular orientation of a syringe during pre-shipping storage thereof, in accordance with the present methods, varying the orientation of the syringe during shipping following such pre-shipping storage can mean maintaining the syringe in a shipping orientation that represents an angular deviation from the orientation during storage of about 45 to about 135 degrees. For example, the orientation of the syringe during shipping may vary from the orientation of the syringe during pre-shipping storage by about 45, 50, 55, 55, 60, 65, 70, 75, 80, 85, 90, 95, 100, 105, 110, 115, 120, 125, 130, or 135 degrees.

For example, the orientation of the syringe during shipping may be substantially horizontal. This is especially suitable when the orientation of the syringe during pre-shipping storage was tip-up or tip-down (wherein the "tip" of the syringe refers to the portion of the syringe to which a needle is attached for purposes of injection). A substantially horizontal orientation may refer to an orientation in which the syringe is at an angle that is closer to 0° than to 90° relative to the applicable reference point, such as the ground, normal to the force of gravity, or the floor of the vehicle in which the syringe is shipped. For example, a substantially horizontal orientation may refer to an orientation that is at 0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 3, 34, 35, 36, 37, 38, 39, 40, 41, 42, 43, or 44 degrees relative to the pertinent reference point.

In other embodiments, the orientation of the syringe during shipping may be substantially tip up. This represents a suitable shipping orientation when the orientation of the syringe during pre-shipping storage was tip-down or substantially horizontal. A tip up orientation may refer to an orientation in which the syringe is at an angle such that the tip is closer to 90° than to 0° relative to the applicable reference point, such as the ground, normal to the force of gravity, or the floor of the vehicle in which the syringe is shipped. For example, a tip up orientation may refer to an orientation that is 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, or 46 degrees relative to the pertinent reference point.

In other embodiments, the orientation of the syringe during shipping may be substantially tip down. This represents a suitable shipping orientation when the orientation of the syringe during pre-shipping storage was tip-up or substantially horizontal. A tip down orientation may refer to an orientation wherein the syringe is flipped 180° relative to one of the tip up orientations described herein.

Regardless of the particular orientation during shipping, "maintaining" an orientation preferably means that the acceptable angle(s) apply for the majority of the time during the shipping process. Ideally, when a substantially horizontal orientation during shipping is desired, the syringe is maintained during shipping at an angle that is always normal to the force of gravity, but, as a practical matter, variations in orientation during shipping inevitably occur due to changes in the orientation of the vehicle in which the syringe is shipped. For example, the orientation of a syringe may be normal to the force of gravity when a truck onto which the syringe is loaded for shipping is at rest on flat topography, but this orientation changes when the truck climbs or descends a hill during the shipping process. Thus, a useful reference point can be the floor of the shipping vehicle rather than the force of gravity, and preferably the syringe is maintained at an orientation that is substantially parallel to the floor of the vehicle during shipping.

Maintaining a particular orientation during shipping of the syringe may comprise loading the syringe onto a shipping vehicle in the desired orientation, monitoring the syringe during shipping to confirm maintenance of the desired orientation, or both. Loading the syringe onto a shipping vehicle in the desired orientation refers to the manner in which the package that houses the syringe is placed onto the shipping vehicle, with the intention that the orientation at the time that the package is placed onto the shipping vehicle is not deliberately changed during the shipping process. Monitoring the syringe during shipping to confirm maintenance of the desired orientation can include direct or indirect observation by a person, by an automatic system that is programmed to confirm compliance with the desired orientation, or a combination of these. Direct observation by a person can include visual inspection by a person of the packaging that houses the syringe. Indirect observation can include the use of a sensor that is attached to or otherwise enables monitoring of the syringe, the package containing the syringe, or both. The sensor can, for example, be capable of acquiring and transmitting information concerning the orientation of the syringe and/or package to a human observer, who determines if the transmitted information indicates that the syringe is being maintained in the required orientation during the shipping process. The sensors can also be capable of conveying an alarm or some other notification if the orientation of the container or package has deviated from the appropriate orientation, for example, if the container/package has shifted during shipping. In one embodiment, the particular orientation, or the desired orientation, is substantially horizontal.

Human monitors or sensors that can detect information concerning the orientation of the syringe can provide a direct determination of the orientation of the syringe, or can do so indirectly, by determining the orientation of the package housing the syringe. For example, markings on the outside of the package can provide a visual cue to a sensor or a human monitor that indicates a corresponding orientation of the syringe that is housed within the package. Accordingly, the syringe may be housed in a container (package) comprising an outer surface that bears instructions or markings that enable the maintenance of the container during shipping in an orientation that corresponds to the orientation of the syringe that is desired (e.g., a substantially horizontal orientation). In some embodiments, the instructions may be provided in appropriate languages, depending on the origin, personnel that are conducting the shipping, and destination of the syringe. In some embodiments, the markings on the outer surface of the container may be an arrow indicating which side of the container should be orientated at the top, at the bottom, or to the side, as appropriate. When there is compliance with the instructions or markings, a syringe that is housed within the container will be oriented correctly in accordance with the present methods.

The shipping of the syringe may occur by any required means of transportation, such as airship (airplane, helicopter, or the like), truck, boat, railroad, or by any combination of these means that may occur from the point of shipping from the drug manufacturing facility to the health care facility where administration occurs. The total duration of the shipping can be any period that is required to convey the syringe from the initial storage location to a second location, such as to a health care facility. For example, the duration of the shipping may be about 1, 2, 3, 4, 5, 6, 7, 8, 9, 10, 11, 12, 13, 14, or 15 hours. The shipping process can involve periods of time during which the syringe is being conveyed, with one or more intervals during which the syringe is not being conveyed, such as at a temporary storage depot prior to a further interval of conveyance. For purposes of the present disclosure, the duration of the shipping can, but does not necessarily need to, refer to the total amount of time that elapses from removal of the syringe from the initial storage facility following manufacture, until the arrival at the facility where administration takes place.

The present methods may further comprise, subsequent to the shipping of the syringe and prior to administration of the drug suspension, maintaining the syringe at a storage location in a deliberately selected orientation, such as in a substantially horizontal orientation. In this context, because the floor of a storage facility is likely to be level and thereby normal to the force of gravity, the substantially horizontal orientation can preferably refer to an angle that is substantially parallel to the floor of the storage facility. This can mean that the angle between the long axis of the syringe and the floor of the storage facility is preferably less than about 20, 15, 10, 9, 8, 7, 6, 5, 4, 3, 2, or 1 degree.

As described above, the present methods facilitate and improve resuspension of the paliperidone palmitate syringe contents. One intended outcome of resuspending the paliperidone palmitate particles is the reduction or removal of residue representing non-resuspended paliperidone palmitate within the tip of the syringe. To the extent that resuspension is incomplete, non-resuspended paliperidone palmitate can remain within the tip of the syringe following administration, and thereby represents undelivered drug and is an indicator of an incomplete administration. Minimizing the amount of residue representing non-resuspended paliperidone palmitate that remains within the syringe tip following administration represents a further beneficial outcome of the presently disclosed methods. For example, in accordance with the present methods, the syringe tip can contain no more than about 3, 2.5, 2, 1.5, 1, or 0.5 mm of residue representing non-resuspended paliperidone palmitate following administration. In some embodiments, the syringe tip contains about 3, 2.8, 2.6, 2.5, 2.4, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, or zero mm of residue representing non-resuspended palmitate following administration.

The syringe may be of any type and equipped with any needle that are suitable for storage and administration of the paliperidone palmitate injectable suspension. For example, the syringe may have a capacity of 1, 1.25, 1.5, 1.75, 2.0, 2.25, 2.5, 2.75, 2.8, 3, 3.25, 3.5, 3.75, 4, 4.25, 4.5, 4.75, 5, 5.25, 5.5, 5.75, 6, 6.25, 6.5, 6.75, or 7 mL. In some embodiments, the syringe has a capacity of 1, 2.25, 2.8, or 3 mL, and includes a 22 gauge needle that is 1 or 1.5 inches long. In some embodiments, the syringe has a capacity of 5 mL and includes a 20 gauge needle that is 1.5 inches long. With respect to any of the presently disclosed inventions, the volume of the paliperidone palmitate injectable suspension with a syringe may be, for example, 1, 1.25, 1.5, 1.75, 2.0, 2.25, 2.5, 2.75, 2.8, 3, 3.25, 3.5, 3.75, 4, 4.25, 4.5, 4.75, 5, 5.25, 5.5, 5.75, 6, 6.25, 6.5, 6.75, or 7 mL.

The present methods can further comprise the step of administering the suspension from the syringe (i.e., that had been maintained in a desired orientation during shipping) to a patient. In some embodiments, the desired orientation is substantially horizontal. Administration of the suspension should be performed, for example, in accordance with the protocols described on the label of the aforementioned commercially available paliperidone palmitate extended release injectable suspension products. Although the present methods mitigate certain instances of failure by health care personnel to adhere precisely to the recommended steps prior to and during administration of paliperidone palmitate extended release injectable suspension, it is still advisable for the administration of the suspension from the syringe according to the present methods to adhere to the labeling protocols.

At the same time, the present methods enable a reduction of the force required for injection of the paliperidone palmitate extended release injectable suspension from a syringe that has been maintained in a substantially horizontal orientation during shipping of the syringe. Accordingly, the present disclosure embraces methods for reducing a force required for injection of a paliperidone palmitate extended release injectable suspension. For example, the force required for injection from the syringe may be about 5-60% less than a force required for injection of a paliperidone palmitate extended-release injectable suspension from a syringe that was not maintained in a substantially horizontal orientation during shipping of the syringe. The force required for injection from the syringe may be, for example, about 5, 10, 15, 20, 25, 30, 35, 40, 45, 50, 55, or 60% less than a force required for injection of a paliperidone palmitate extended-release injectable suspension from a syringe that was not maintained in a substantially horizontal orientation during shipping of the syringe. In some embodiments, the force required for injection from the syringe may be about 10-55, 15-50, 20-50, 25-45, or 30-40% less than a force required for injection of a paliperidone palmitate extended-release injectable suspension from a syringe that was not maintained in a substantially horizontal orientation during shipping of the syringe. In addition, and at the same time, the present methods enable a reduction of the force required for injection of the paliperidone palmitate extended release injectable suspension from a syringe that has been maintained in an orientation during shipping that varies from the orientation of the syringe during pre-shipping storage, such as in a substantially horizontal orientation during shipping of the syringe when the orientation during pre-shipping storage was not substantially horizontal. Accordingly, the present disclosure embraces methods for reducing a force required for injection of a paliperidone palmitate extended release injectable suspension. For example, the force required for injection from the syringe may be about 5-60% less than a force required for injection of a paliperidone palmitate extended-release injectable suspension from a syringe that was not maintained in an orientation during shipping that varies from the orientation of the syringe during pre-shipping storage. The force required for injection from the syringe may be, for example, about 5, 10, 15, 20, 25, 30, 35, 40, 45, 50, 55, or 60% less than a force required for injection of a paliperidone palmitate extended-release injectable suspension from a syringe that was not maintained in an orientation during shipping that varies from the orientation of the syringe during pre-shipping storage. In some embodiments, the force required for injection from the syringe may be about 10-55, 15-50, 20-50, 25-45, or 30-40% less than a force required for injection of a paliperidone palmitate extended-release injectable suspension from a syringe that was not maintained in an orientation during shipping that varies from the orientation of the syringe during pre-shipping storage.

In absolute terms, the force required for injection of the paliperidone palmitate extended release injectable suspension from the syringe may be about 10-25 Newtons less than a force required for injection of a paliperidone palmitate extended-release injectable suspension from a syringe that was not maintained in a substantially horizontal orientation during shipping of the syringe. The force required for injection from the syringe may be, for example, about 10, 11, 12, 13, 14, 15, 16, 17, 18, 19, 20, 21, 22, 23, 24, or 25 Newtons less than a force required for injection of a paliperidone palmitate extended-release injectable suspension from a syringe that was not maintained in a substantially horizontal orientation during shipping of the syringe. The amount of force that is actually required for injection of the paliperidone palmitate extended release injectable suspension from the syringe may be, for example, about 10-25 Newtons. Thus, the force required for injection from the syringe may be, for example, about 10, 11, 12, 13, 14, 15, 16, 17, 18, 19, 20, 21, 22, 23, 24, or 25 Newtons. In addition, in absolute terms, the force required for injection of the paliperidone palmitate extended release injectable suspension from the syringe may be about 5-25 Newtons less than a force required for injection of a paliperidone palmitate extended-release injectable suspension from a syringe that was not maintained in an orientation during shipping that varies from the orientation of the syringe during pre-shipping storage. The force required for injection from the syringe may be, for example, about 5, 6, 7, 8, 9, 10, 11, 12, 13, 14, 15, 16, 17, 18, 19, 20, 21, 22, 23, 24, or 25 Newtons less than a force required for injection of a paliperidone palmitate extended-release injectable suspension from a syringe that was not maintained in an orientation during shipping that varies from the orientation of the syringe during pre-shipping storage. The amount of force that is actually required for injection of the paliperidone palmitate extended release injectable suspension from the syringe may be, for example, about 10-25 Newtons. Thus, the force required for injection from the syringe may be, for example, about 10, 11, 12, 13, 14, 15, 16, 17, 18, 19, 20, 21, 22, 23, 24, or 25 Newtons.

The present methods may further comprise assessing the amount of force that is required to complete an injection of the paliperidone palmitate extended release injectable suspension from the syringe. The assessment may be performed using any available measurement technique.

The present methods may also or alternatively comprise assessing whether an injection of the paliperidone palmitate extended-release injectable suspension from the syringe is complete. The assessment may include measuring the amount of non-resuspended paliperidone palmitate within the tip of the syringe exceeds a certain value, such as, for example, about 4, 3.75, 3.5, 3.25, 3, 2.75, 2.5, 2.25, 2, 1.75, 1.5, 1.25, 1, 0.75, 0.5, or 0.25 mm in length.

Also disclosed herein are methods for improving resuspendability of a paliperidone palmitate extended release injectable suspension within a syringe comprising maintaining the syringe in a substantially horizontal orientation during storage of the syringe. Storage of the syringe may occur prior to, or following, shipping of the syringe. In certain embodiments, the storage of the syringe occurs following shipping of the syringe, e.g., at a location that corresponds to the health care facility where administration of the paliperidone palmitate occurs. These methods may be performed independently from or in conjunction with the above-described methods of improving resuspendability that comprise maintaining the syringe in a substantially horizontal orientation during shipping. In other words, the syringe may be stored in the substantially horizontal orientation, shipped in the substantially horizontal orientation, or both shipped and stored in the substantially horizontal orientation. Storage of the syringe in a substantially horizontal orientation may be facilitated by markings or other instructions on the packaging or container that houses the syringe, and such markings may be the same as, or different from, markings or instructions that are intended to ensure maintenance of a substantially horizontal orientation during shipping. As in the case of the methods comprising maintaining the substantially horizontal orientation during shipping, the present methods may further comprise monitoring in order to ensure the maintenance of the substantially horizontal orientation during storage. Approaches for monitoring may be the same as those described above in connection with the maintenance of the substantially horizontal orientation during shipping. Also disclosed herein are methods for improving resuspendability of a paliperidone palmitate extended release injectable suspension within a syringe comprising maintaining the syringe in an orientation during shipping that varies from the orientation of the syringe during pre-shipping storage, such as in a substantially horizontal orientation during storage of the syringe when the orientation during pre-shipping storage was not substantially horizontal. Storage of the syringe may occur prior to, or following, shipping of the syringe. In certain embodiments, the storage of the syringe occurs following shipping of the syringe, e.g., at a location that corresponds to the health care facility where administration of the paliperidone palmitate occurs. These methods may be performed independently from or in conjunction with the above-described methods of improving resuspendability that comprise maintaining the syringe in an orientation during shipping that varies from the orientation of the syringe during pre-shipping storage. In other words, the syringe may be shipped in the substantially horizontal orientation, and subsequently stored in the substantially horizontal orientation, or both shipped and stored in the substantially horizontal orientation. Storage of the syringe in a particular orientation may be facilitated by markings or other instructions on the packaging or container that houses the syringe, and such markings may be the same as, or different from, markings or instructions that are intended to ensure maintenance of a desired orientation during shipping. As in the case of the methods comprising maintaining a particular orientation during shipping, the present methods may further comprise monitoring in order to ensure the maintenance of the desired orientation during storage. Approaches for monitoring may be the same as those described above in connection with the maintenance of the desired orientation during shipping.

The present disclosure also provides a population of syringes that respectively contain paliperidone palmitate extended release injectable suspension, wherein each of the syringes have been shipped to a destination, and the syringes were each maintained in a substantially horizontal orientation during shipping of the syringe. Each member of the population of syringes will therefore accrue the benefits described above associated with shipping in a substantially horizontal orientation, including improved resuspendability, less residue in the syringe tip following administration, less force required for administration, and the like. The population of syringes may include about 5, 10, 15, 20, 25, 30, 35, 40, 45, 50, 55, 60, 65, 70, 75, 80, 85, 90, 95, 100, 120, 140, 160, 180, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more than 2000 individual syringes. Each member of the population of syringes may include the syringe types and paliperidone palmitate suspensions otherwise described herein in accordance with the presently disclosed methods. In addition, the present disclosure also provides a population of syringes that respectively contain paliperidone palmitate extended release injectable suspension, wherein each of the syringes have been shipped to a destination, and the syringes were each maintained in an orientation during shipping that varies from the orientation of the syringe during pre-shipping storage, such as in a substantially horizontal orientation during shipping of the syringe when the orientation during pre-shipping storage was not substantially horizontal. Each member of the population of syringes will therefore accrue the benefits described above associated with shipping in an orientation during shipping that varies from the orientation of the syringe during pre-shipping storage, including improved resuspendability, less residue in the syringe tip following administration, less force required for administration, and the like. The population of syringes may include about 5, 10, 15, 20, 25, 30, 35, 40, 45, 50, 55, 60, 65, 70, 75, 80, 85, 90, 95, 100, 120, 140, 160, 180, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more than 2000 individual syringes. Each member of the population of syringes may include the syringe types and paliperidone palmitate suspensions otherwise described herein in accordance with the presently disclosed methods.

Also provided herein are pharmaceutical products that comprise a paliperidone palmitate extended-release injectable suspension within a syringe for administration to a patient suffering from schizophrenia, wherein the syringe has undergone pre-shipping storage and has been shipped, and wherein the syringe has been maintained in an orientation during the shipping that varied from the orientation of the syringe during pre-shipping storage. The respective characteristics of the paliperidone palmitate extended-release injectable suspension, the syringe, the pre-shipping storage conditions, the orientation of the syringe during pre-shipping storage, the shipping conditions, and the orientation of the syringe during shipping may be in accordance with any of the embodiments described above in connection with the inventive methods for improving resuspendability of a paliperidone palmitate extended-release injectable suspension within a syringe and the inventive populations of syringes.

For example, the syringe may have been housed within a container comprising an outer surface that included instructions for maintaining the container during shipping in an orientation that corresponds to the desired orientation of the syringe. In some embodiments, the syringe was housed within a container comprising an outer surface that included markings that indicated an orientation of the container that corresponds to maintaining the desired orientation of the syringe.

Following the shipping, the syringe may contain no more than about 1.5 mm or no more than about 1 mm of residue representing non-resuspended paliperidone palmitate after injection of the suspension. For example, the syringe may contain about 1.5, 1.4, 1.3, 1.2, 1.1, 1.0, 0.9, 0.8, 0.7, 0.6, 0.5, 0.4, 0.3, 0.2, or 0.1 mm of residue representing non-resuspended paliperidone palmitate after injection of the suspension.

The paliperidone palmitate extended-release injectable suspension within the syringe may contain about 273, 410, 546, or 819 mg of paliperidone palmitate. In other embodiments, the suspension contains about 1092 or 1560 mg of paliperidone palmitate.

The shipping orientation may have varied from the orientation of the syringe during pre-shipping storage by about 45 degrees to about 135 degrees. For example, the orientation of the syringe during shipping may have varied from the orientation of the syringe during pre-shipping storage by about 45, 50, 55, 55, 60, 65, 70, 75, 80, 85, 90, 95, 100, 105, 110, 115, 120, 125, 130, or 135 degrees In some embodiments of the presently disclosed pharmaceutical product, the pre-shipping storage orientation was tip down. In some embodiments of the presently disclosed pharmaceutical product, the shipping orientation was substantially horizontal. In certain embodiments of the presently disclosed pharmaceutical product, the pre-shipping storage orientation was tip down, and the shipping orientation was tip up or substantially horizontal. In other embodiments, the pre-shipping storage orientation was tip down, and the shipping orientation was substantially horizontal. In other embodiments, the pre-shipping storage was tip down, and the shipping orientation was tip up.

The present disclosure also provides methods of treating schizophrenia comprising administering to a patient suffering from schizophrenia a paliperidone palmitate extended-release injectable suspension from a syringe, wherein the syringe has undergone pre-shipping storage and has been shipped, and wherein the syringe was maintained in an orientation during the shipping that varied from the orientation of the syringe during pre-shipping storage. The present disclosure also provides a paliperidone palmitate extended-release injectable suspension for use in methods of treating schizophrenia, wherein these methods comprise administering to a patient suffering from schizophrenia the paliperidone palmitate extended-release injectable suspension from a syringe, wherein the syringe has undergone pre-shipping storage and has been shipped, and wherein the syringe was maintained in an orientation during the shipping that varied from the orientation of the syringe during pre-shipping storage. Administration of the suspension should be performed, for example, in accordance with the protocols described on the label of the aforementioned commercially available paliperidone palmitate extended release injectable suspension products. Although the present methods mitigate certain instances of failure by health care personnel to adhere precisely to the recommended steps prior to and during administration of paliperidone palmitate extended release injectable suspension, it is still advisable for the administration of the suspension from the syringe according to the present methods to adhere to the labeling protocols.

With respect to the presently disclosed methods of treating schizophrenia, the respective characteristics of the paliperidone palmitate extended-release injectable suspension, the syringe, the pre-shipping storage conditions, the orientation of the syringe during pre-shipping storage, the shipping conditions, and the orientation of the syringe during shipping may be in accordance with any of the embodiments described above in connection with the inventive methods for improving resuspendability of a paliperidone palmitate extended-release injectable suspension within a syringe and the inventive populations of syringes.

For example, the syringe may have been housed within a container comprising an outer surface that included instructions for maintaining the container during shipping in an orientation that corresponds to the desired orientation of the syringe. In some embodiments, the syringe was housed within a container comprising an outer surface that included markings that indicated an orientation of the container that corresponds to maintaining the desired orientation of the syringe.

Following the shipping, the syringe may contain no more than about 1.5 mm or no more than about 1 mm of residue representing non-resuspended paliperidone palmitate after injection of the suspension. For example, the syringe may contain about 1.5, 1.4, 1.3, 1.2, 1.1, 1.0, 0.9, 0.8, 0.7, 0.6, 0.5, 0.4, 0.3, 0.2, or 0.1 mm of residue representing non-resuspended paliperidone palmitate after injection of the suspension.

The paliperidone palmitate extended-release injectable suspension within the syringe may contain about 273, 410, 546, or 819 mg of paliperidone palmitate. In other embodiments, the suspension contains about 1092 or 1560 mg of paliperidone palmitate.

The shipping orientation may have varied from the orientation of the syringe during pre-shipping storage by about 45 degrees to about 135 degrees. For example, the orientation of the syringe during shipping may have varied from the orientation of the syringe during pre-shipping storage by about 45, 50, 55, 55, 60, 65, 70, 75, 80, 85, 90, 95, 100, 105, 110, 115, 120, 125, 130, or 135 degrees In some embodiments of the presently disclosed methods of treating schizophrenia, the pre-shipping storage orientation was tip down. In some embodiments of the presently disclosed methods of treating schizophrenia, the shipping orientation was substantially horizontal. In certain embodiments of the presently disclosed methods, the pre-shipping storage orientation was tip down, and the shipping orientation was tip up or substantially horizontal. In other embodiments, the pre-shipping storage orientation was tip down, and the shipping orientation was substantially horizontal. In other embodiments, the pre-shipping storage was tip down, and the shipping orientation was tip up.

The present disclosure also provides the use of a paliperidone palmitate extended-release injectable suspension in the manufacture of a medicament for treating schizophrenia, wherein the paliperidone palmitate extended-release injectable suspension is prepared for administration from a syringe, wherein the syringe has undergone pre-shipping storage and has been shipped, and wherein the syringe was maintained in an orientation during the shipping that varied from the orientation of the syringe during pre-shipping storage. Administration of the suspension should be performed, for example, in accordance with the protocols described on the label of the aforementioned commercially available paliperidone palmitate extended release injectable suspension products. Although the present uses mitigate certain instances of failure by health care personnel to adhere precisely to the recommended steps prior to and during administration of paliperidone palmitate extended release injectable suspension, it is still advisable for the administration of the suspension from the syringe according to the present uses to adhere to the labeling protocols.

With respect to the presently disclosed uses, the respective characteristics of the paliperidone palmitate extended-release injectable suspension, the syringe, the pre-shipping storage conditions, the orientation of the syringe during pre-shipping storage, the shipping conditions, and the orientation of the syringe during shipping may be in accordance with any of the embodiments described above in connection with the inventive methods for improving resuspendability of a paliperidone palmitate extended-release injectable suspension within a syringe and the inventive populations of syringes.

For example, the syringe may have been housed within a container comprising an outer surface that included instructions for maintaining the container during shipping in an orientation that corresponds to the desired orientation of the syringe. In some embodiments, the syringe was housed within a container comprising an outer surface that included markings that indicated an orientation of the container that corresponds to maintaining the desired orientation of the syringe.

Following the shipping, the syringe may contain no more than about 1.5 mm or no more than about 1 mm of residue representing non-resuspended paliperidone palmitate after injection of the suspension. For example, the syringe may contain about 1.5, 1.4, 1.3, 1.2, 1.1, 1.0, 0.9, 0.8, 0.7, 0.6, 0.5, 0.4, 0.3, 0.2, or 0.1 mm of residue representing non-resuspended paliperidone palmitate after injection of the suspension.

The paliperidone palmitate extended-release injectable suspension within the syringe may contain about 273, 410, 546, or 819 mg of paliperidone palmitate. In other embodiments, the suspension contains about 1092 or 1560 mg of paliperidone palmitate.

The shipping orientation may have varied from the orientation of the syringe during pre-shipping storage by about 45 degrees to about 135 degrees. For example, the orientation of the syringe during shipping may have varied from the orientation of the syringe during pre-shipping storage by about 45, 50, 55, 55, 60, 65, 70, 75, 80, 85, 90, 95, 100, 105, 110, 115, 120, 125, 130, or 135 degrees In some embodiments of the presently disclosed uses, the pre-shipping storage orientation was tip down. In some embodiments of the presently disclosed uses, the shipping orientation was substantially horizontal. In certain embodiments of the presently disclosed uses, the pre-shipping storage orientation was tip down, and the shipping orientation was tip up or substantially horizontal. In other embodiments, the pre-shipping storage orientation was tip down, and the shipping orientation was substantially horizontal. In other embodiments, the pre-shipping storage was tip down, and the shipping orientation was tip up.

The invention is further defined with reference to the following numbered clauses:

1. A method for improving resuspendability of a paliperidone palmitate extended-release injectable suspension within a syringe comprising maintaining the syringe in a substantially horizontal orientation during shipping of the syringe.

2. The method according to clause 1, wherein maintaining the syringe in the substantially horizontal orientation comprises loading the syringe onto a shipping vehicle in the substantially horizontal orientation, monitoring the syringe during shipping to confirm maintenance of the substantially horizontal orientation, or both.

3. The method according to clause 1 or clause 2, further comprising housing the syringe within a container comprising an outer surface that bears instructions for maintaining the container during shipping in an orientation that corresponds to the orientation of the syringe that is substantially horizontal.

4. The method according to any preceding clause, further comprising housing the syringe within a container comprising an outer surface that bears markings that indicate an orientation of the container that corresponds to maintaining the orientation of the syringe that is substantially horizontal.

5. The method according to any preceding clause, further comprising, subsequent to shipping of the syringe, maintaining the syringe at a storage location in a substantially horizontal orientation.

6. The method according to any preceding clause, wherein the syringe is shipped by airplane, truck, boat, or railroad.

7. The method according to any preceding clause, wherein, following the shipping, the syringe contains no more than about 1.5 mm of residue representing non-resuspended paliperidone palmitate after administration.

8. The method according to any preceding clause, wherein, following the shipping, the syringe contains no more than about 1 mm of residue representing non-resuspended paliperidone palmitate.

9. The method according to any preceding clause, wherein the syringe has a capacity of 1 mL, 2.25 mL, 2.8 mL, or 3 mL and includes a 22 gauge needle that is 1 or 1.5 inches long.

10. The method according to any one of clauses 1-8, wherein the syringe has a capacity of 5 mL, and includes a 20 gauge needle that is 1.5 inches long.

11. The method according to any one of clauses 1-10, wherein the suspension contains about 273, 410, 546, or 819 mg of paliperidone palmitate.

12. The method according to any one of clauses 1-10, wherein the suspension contains about 1092 or 1560 mg of paliperidone palmitate.

13. The method according to any one of clauses 1-12, further comprising administering the suspension from the syringe to a patient.

14. A method for reducing a force required for injection of a paliperidone palmitate extended-release injectable suspension from a syringe comprising maintaining the syringe in a substantially horizontal orientation during shipping of the syringe.

15. The method according to clause 14, wherein the force required for injection from the syringe is about 20% to about 50% less than a force required for injection of a paliperidone palmitate extended-release injectable suspension from a syringe that was not maintained in a substantially horizontal orientation during shipping of the syringe.

16. The method according to clause 14 or clause 15, wherein the force required for injection from the syringe is about 10-25 Newtons less than a force required for injection of a paliperidone palmitate extended-release injectable suspension from a syringe that was not maintained in a substantially horizontal orientation during shipping of the syringe.

17. The method according to any one of clauses 14-16, wherein the force required for injection from the syringe is about 10-25 Newtons.

18. The method according to any one of clauses 14-17, further comprising assessing the force required to complete an injection of the paliperidone palmitate extended-release injectable suspension from the syringe.

19. A method for reducing the likelihood of incomplete injection of a paliperidone palmitate extended-release injectable suspension from a syringe comprising maintaining the syringe in a substantially horizontal orientation during shipping of the syringe.

20. The method according to clause 19, further comprising assessing whether an injection of the paliperidone palmitate extended-release injectable suspension from the syringe is complete.

21. A method for improving resuspendability of a paliperidone palmitate extended-release injectable suspension within a syringe comprising maintaining the syringe in a substantially horizontal orientation during storage of the syringe.

22. The method according to clause 21, wherein said storage occurs following shipping of the syringe.

23. A population of syringes that respectively contain paliperidone palmitate extended release injectable suspension, wherein each of the syringes have been shipped to a destination, and the syringes were each maintained in a substantially horizontal orientation during shipping of the syringe.

24. The population according to clause 22, comprising at least 100 individual syringes

EXAMPLES

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions. Unless otherwise noted, references to PP6M in the examples refer to the formulation in Example 2.

Example 1—Three Month Extended Release Formulation (PP3M)

Table 1 below includes an exemplary three-month extended release formulation (PP3M) of 200 mg/mL eq. paliperidone suitable for intramuscular (IM) injection.

TABLE 1

| PP3M | |
|---|---|
| Component | Concentration (mg/mL) |
| Paliperidone Palmitate | 312 |
| Polysorbate 20 | 10 |
| Polyethylene Glycol 4000 | 75 |
| Citric Acid Monohydrate | 7.5 |
| Sodium Dihydrogen Phosphate Monohydrate | 6 |
| Sodium Hydroxide | 5.4 |
| Water for Injection | q.s. ad 1 mL |

The PP3M can be provided in a prefilled syringe, with dosage strengths ranging from 175 mg eq. to 525 mg eq. obtained by filling the syringes with different volumes of a 200 mg/mL eq. bulk suspension. Table 2 shows the different dosage strengths, including syringe size, and nominal fill volume.

TABLE 2

| PP3M Dosage Strengths with Syringe Size and Fill Volume | | | |
|---|---|---|---|
| Dose as Paliperidone Palmitate (mg) | Dose Equivalent as Paliperidone (mg) | Syringe Size | Nominal Fill Volume (mL) |
| 273 | 175 | 1 mL Long | 0.875 |
| 410 | 263 | 2.25 mL | 1.315 |

TABLE 2-continued

PP3M Dosage Strengths with Syringe Size and Fill Volume

| Dose as Paliperidone Palmitate (mg) | Dose Equivalent as Paliperidone (mg) | Syringe Size | Nominal Fill Volume (mL) |
|---|---|---|---|
| 546 | 350 | 2.25 mL | 1.750 |
| 819 | 525 | 2.8 mL | 2.625 |

Table 3 describes the syringe components used to package the PP3M,

TABLE 3

Syringe Components for PP3M

| Component | Description |
|---|---|
| Syringe Barrel | Transparent Cyclic Olefin Copolymer (COC) with Integrated Luer Lock Sizes of 1 mL Long, 2.25 mL or 2.8 mL |
| Tip Cap | Bromobutyl Rubber, Dark Grey |
| Plunger Stopper | FluoroTec © Coated Bromobutyl Rubber, Dark Grey (1 mL Long used for 1 mL Long syringe; and 1-3 mL used for 2.25 mL syringe and 2.8 mL syringe) |

Example 2—Six Month Extended Release Formulation (PP6M)

Table 4 below includes an exemplary six-month extended release formulation (PP6M) of 200 mg/mL eq. paliperidone palmitate suitable for intramuscular (IM) injection

TABLE 4

PP6M

| Component | Concentration (mg/mL) | Unit Dose (mg/syringe in 3.5 mL Dose) | Unit Dose (mg/syringe in 5.0 mL Dose) |
|---|---|---|---|
| Paliperidone Palmitate | 312 | 1092 | 1560 |
| Polysorbate 20 | 10 | 35 | 50 |
| Polyethylene Glycol 4000 | 75 | 262.5 | 375 |
| Citric Acid Monohydrate | 7.5 | 26.25 | 37.5 |
| Sodium Dihydrogen Phosphate Monohydrate | 6 | 21 | 30 |
| Sodium Hydroxide | 5.4 | 18.9 | 27 |
| Water for Injection | q.s. ad 1.0 mL | q.s. ad 3.5 mL | q.s. ad 5.0 mL |

The PP6M can be provided in a prefilled syringe, with dosage strengths ranging from 700 mg eq. to 1000 mg eq. obtained by filling the syringes with different volumes of a 200 eq. bulk suspension. Table 5 shows the different dosage strengths, including syringe size, and nominal fill volume.

TABLE 5

PP6M Dosage Strengths with Syringe Size and Fill Volume

| Dose as Paliperidone Palmitate (mg) | Dose Equivalent as Paliperidone (mg) | Syringe Size | Nominal Fill Volume (mL) |
|---|---|---|---|
| 1092 | 700 | 5 mL | 3.5 |
| 1560 | 1000 | 5 mL | 5.0 |

Table 6 describes the syringe components used to package the six-month extended release formulation.

TABLE 6

Syringe Components for PP6M

| Component | Description |
|---|---|
| Syringe Barrel | Transparent Cyclic Olefin Copolymer (COC) with Integrated Luer Lock |
| Tip Cap | Bromobutyl Rubber |
| Plunger Stopper | Bromobutyl Rubber |
| Plunger Rod | Polypropylene |
| Backstop (aka Finger Flange) | Homopolypropylene |

Example 3—Storage Conditions Prior to Shipping

Stability studies were performed with process performance qualification (PPQ) batches of PP6M in five different orientations prior to shipping: horizontal, tip down +45 degrees, tip up −45 degrees, tip down +45 degrees and tip down −45 degrees. The following test results were obtained with respect to syringes that were stored following manufacture, but that were not shipped prior to testing. Sensor testing with 5 seconds of shaking was performed at two different temperatures: 25° C. and 30° C. The results from this experiment are provided in Table 7:

TABLE 7

| | | PPQ I | | PPQ II | | PPQ III | |
|---|---|---|---|---|---|---|---|
| | | 3.5 ml fill | 5 ml fill | 3.5 ml fill | 5 ml fill | 3.5 ml fill | 5 ml fill |
| HORIZONTAL | 9 M 25° C. | 0 | 0 | 0 | 0 | 0 | 1 mm |
| | 9 M 30° C. | 0 | 0 | 0 | 0 | 2 mm | 2 mm, 2 mm |
| TIP UP (blister: ↑) | 9 M 25° C. | 0 | 0 | 0 | 0 | 0 | 1 mm |
| | 9 M 30° C. | 0 | 0 | 0 | 0 | 0 | 0 |
| TIP UP (blister: ↗) | 9 M 25° C. | NT | NT | NT | NT | NT | 0 |
| | 9 M 30° C. | NT | NT | NT | NT | NT | 0 |
| TIP DOWN (blister: ↓) | 9 M 25° C. | 0 | 1 mm | 0 | 2 mm | NT | 0 |
| | 9 M 30° C. | 0 | 0 | 0 | 1 mm, 2 mm | NT | 0 |

TABLE 7-continued

|  |  | PPQ I | | PPQ II | | PPQ III | |
| --- | --- | --- | --- | --- | --- | --- | --- |
|  |  | 3.5 ml fill | 5 ml fill | 3.5 ml fill | 5 ml fill | 3.5 ml fill | 5 ml fill |
| TIP DOWN (blister: ↘) | 9 M 25° C. | NT | NT | NT | NT | NT | 0 |
|  | 9 M 30° C. | NT | NT | NT | NT | NT | 0 |

Note:
PPQ III horizontal samples are blistered (housed in a blister package), PPQII and PPQI horizontal samples are not blistered.
9 M = nine month storage period.
NT = not tested.

Injectability testing was performed via manual injection, using a sensor on the thumb pad of the plunger rod to record force (Newton) over time (seconds). Force injection profiles for the samples in PPQ I and PPQ II after 5 seconds of vigorous shaking are illustrated in FIGS. 1A-1F.

The results suggested that product stored in any position prior to shipping could be resuspended with a normal amount of force, i.e., that the force required to expel syringe contents was not related to the storage position before shipping occurs. The different storage positions give comparable results indicating that the position in which the syringe is stored prior to shipping is not critical when shaken for at least 5 seconds. Complete injection could be performed with acceptable injection forces.

After this experiment, it became apparent that the storage position of the product during stability testing and prior to shipping was not an important determinant of resuspendability. As described below in Example 4, it was found that the shipment orientation was much more important than pre-shipping storage orientation.

Example 4—Orientation During Simulated Shipping

Following a period of storage in a tip down orientation at the manufacturing facility, syringes containing the PP6M formulation were subjected to a simulated shipping experiment with vibrations corresponding to Level I and Level II vibrations as defined by AS™ D4169-16 for simulated air shipments. These are the highest levels of vibration during air shipment and exceed vibration levels defined for shipments by truck. The resuspendability and injectability of the PP6M formulation after the simulated shipment was tested with no or only 5 seconds of shaking (shorter than defined by instructions for use (IFU), which are consistent with the instructions provided on the label for the INVEGA TRINZA® (PP3M product); IFU for PP6M is 2×15 seconds of shaking, and IFU for PP3M is 1-15 seconds of shaking)) to increase the sensitivity of the test of detecting differences. A summary of the residue leftover in the syringes, and the maximum force required to empty the syringes to that point are provided below in Table 8:

TABLE 8

Residue after Preparations According to Instructions for Use (With Pull Back and Deaeration)

| Position | Resusp. | 2 hours level II | 2 h(II) + 3 hours (I) |
| --- | --- | --- | --- |
| Tip down | NO shaking | 2 mm (36N) | 16 mm (40N) |
|  |  | Cannot be inj. (49N) | 14 mm (37N) |
|  | 5° shaking (4 shakes/s) | 1 mm (35N) | 1 mm (32N) |
|  |  | 0 mm (18N) | 1 mm (30N) |
|  |  | 1 mm (26N) | 1 mm (36N) |
| Horizontal | NO shaking | 0 mm (26N) | 0 mm (34N) |
|  |  | 0 mm (26N) | 0 mm (29N) |
|  | 5° shaking (4 shakes/s) | 0 mm (17N) | 0 mm (19N) |
|  |  | 0 mm (16N) | 0 mm (17N) |
|  |  | 0 mm (18N) | 0 mm (17N) |

Figure 2A:
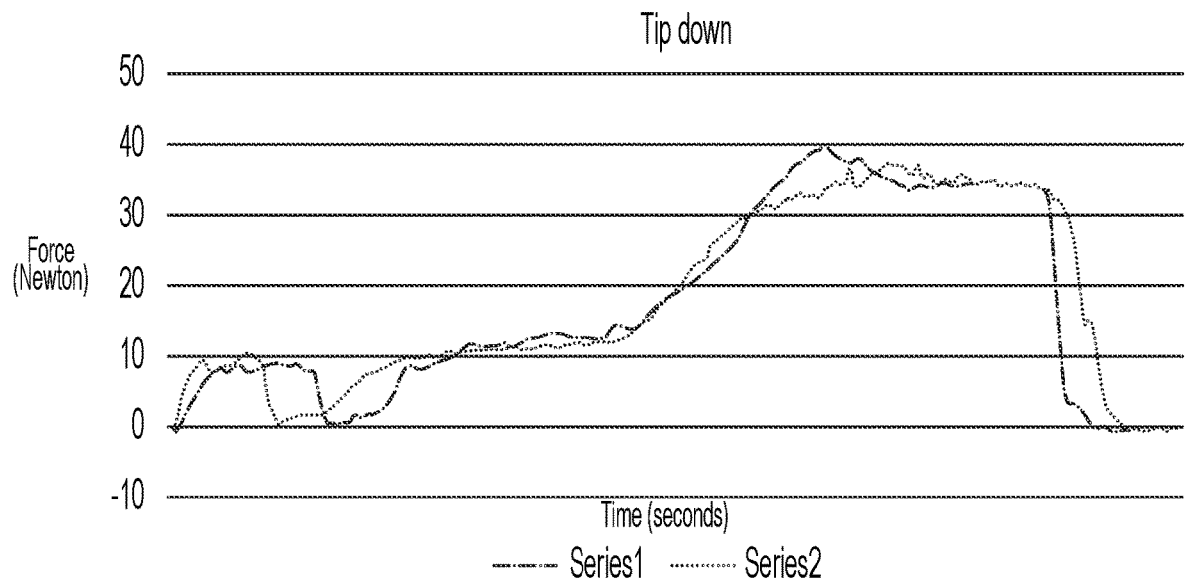
FIGS. 2A-2D provide injection force curves for syringes subjected to vibration experiments while in a horizontal or tip down orientation.
Figure 2B:
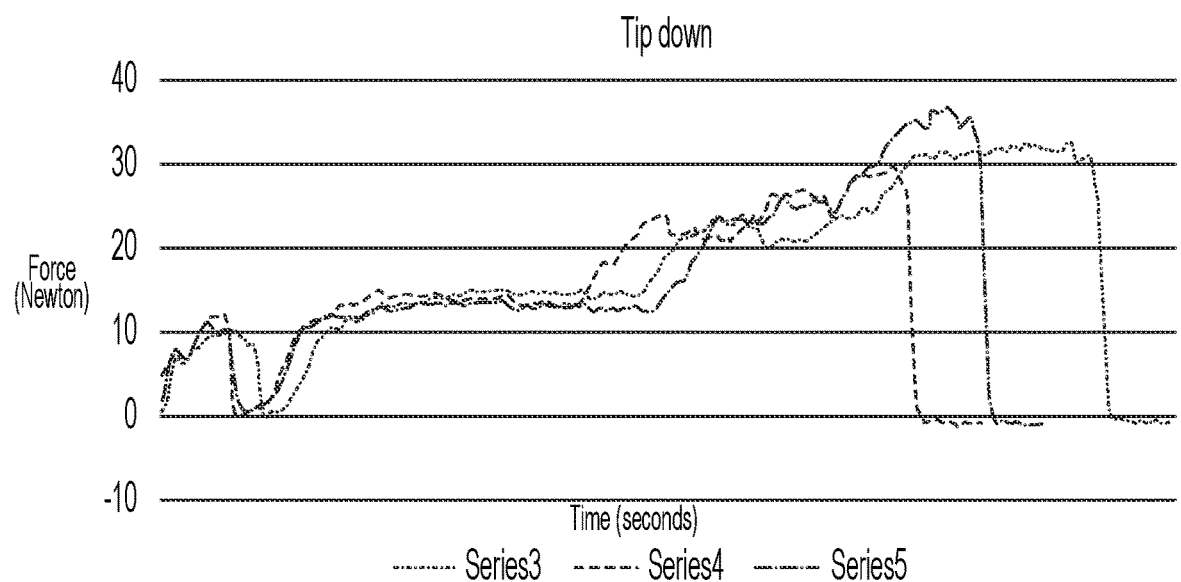
Figure 2C:
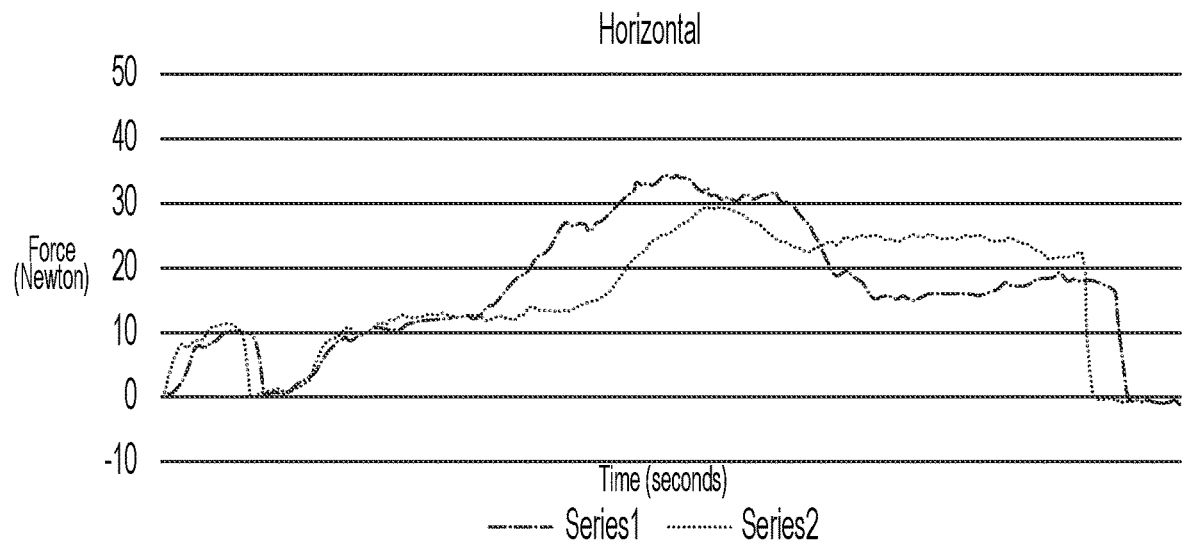
Figure 2D:
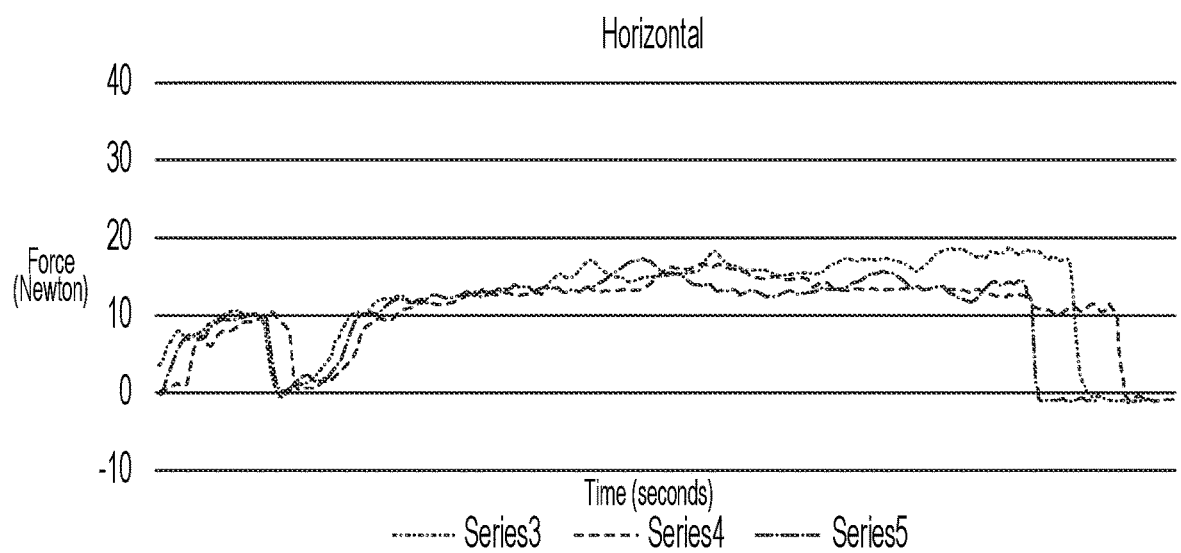

FIGS. 2A-2D provide injection force curves for syringes subjected to vibration experiments while in a horizontal or tip down orientation. Injectability testing was performed via manual injection, using a sensor on the thumb pad of the plunger rod to record force (Newton) over time (seconds). The vibration conditions included two hours of Level II simulated air shipment and three hours of Level I simulated air shipment in accordance with AS™ D4169. FIG. 2A corresponds to a syringe that was in the tip down orientation and was not subjected to shaking prior to injection. FIG. 2B corresponds to a syringe that was in the tip down orientation and was subjected to five seconds of shaking prior to injection. FIG. 2C corresponds to a syringe that was in a horizontal orientation and was not subjected to shaking prior to injection. FIG. 2D corresponds to a syringe that was in a horizontal orientation and was subjected to five seconds of shaking prior to injection.

The results from this experiment confirm that shipment of syringes in the tip-down position following storage in a tip-down orientation can result in the requirement for very high forces in order to express syringe contents, and that the contents of such syringes are not completely resuspended after 5 seconds of shaking. As a practical matter, health care providers will not be pushing up to 30 or 35N, especially when injecting a patient.

However, when syringes were shipped in the horizontal manner after having been stored in a tip-down orientation, injection forces were in the range of 10-20 Newtons, indicating that the product required less shaking for good resuspension to occur. By comparison, the forces required to expel a one-month paliperidone palmitate injectable suspension, which represents a much less concentrated formulation (and thereby a preparation that is much less vulnerable to impaction and thereby having lower resuspension requirements) are in the range of 7-12 Newtons.

Example 5—Varying Orientation of Syringes During Shipping Relative to Orientation During Pre-Shipping Storage Reduces Injection Forces and Post-Injection Residue After initial proof that horizontal orientation of PP6M syringes during shipment leads to improved resuspendability and injectability properties compared to tip down orientation a further study was initiated to assess more in depth the potential impact of different types and duration of shipment and to monitor the behavior of PP6M syringes up to three months after simulated shipment.

For this study, 5 mL syringes PP6M were selected from stability chambers. The 5 mL fill was chosen over the 3.5 mL fill as worst case for resuspendability because of the higher product load in same 5 mL syringe.

Before being exposed to simulated shipment conditions, samples from the different batches, stored in different orientations in the stability chambers but not yet subjected to shipping conditions, were tested for resuspendability/injectability by manually injecting the syringe into a container after 5 seconds poorly shaking. The injectability forces were recorded with a sensor attached to the thumb pad, and the height of the residual product in the syringe was measured. All samples resulted in complete injections with no or an acceptable product residue in the syringe, concluding that the different pre-shipping storage orientation set-ups did not by themselves influence the properties of the suspension, and that the product was easily resuspendable and injectable after 9 months of storage.

Following this initial testing, syringes were transported by car from Beerse, Belgium to a testing facility in Diepenbeek, Belgium and subjected to different shipping simulations ranging from light exposure (1 h truck light) to heavy exposure (4 h air high). Simulated ship testing was performed per AST™ D4169-16. During these shipping simulations, the syringes were positioned either horizontally or tip down. During routine manufacturing, the syringes are stored tip down in tubs after filling typically for a month or more. When a packaging order is issued, the syringes are packed in blister kit and shipped after release. Within a day after the shipping simulation, samples exposed to the different simulated shipping conditions in different orientations were resuspended by rapid shaking for 5 seconds and manually injecting the product into a container, while injection forces were measured with a sensor attached to the thumb pad of the syringe. A shorter time to resuspend the product (5 s instead of 2×15 seconds per IFU) was used for the analysis to increase the sensitivity of the test.

The rest of the syringes was stored horizontally or tip down as per the protocol and the resuspendability/injectability of the syringes was further assessed after one month, two months, or three months of storage.

As also described below, the analysis showed that the orientation of the syringe before shipment relative to the shipping orientation, is an important factor in the resuspension of the product.

In both single shipments and combined truck/air shipments, maintaining the same orientation of the syringes during initial storage and shipment led to more difficult to resuspend syringes resulting in more residual product after only 5 seconds of rapid shaking.

Storage position after shipment and storage time represented factors with only limited impact on the resuspendability of the product.

The data provided in Tables 9-11, infra, demonstrate that when syringes are shipped horizontally following horizontal storage prior to shipping, there is more residual product after 5 seconds of rapid resuspendability and injection, compared to syringes that were stored tip down.

Similarly, syringes stored tip up before shipping and orientated tip down during shipping contained no or very limited residual product after 5 seconds of rapid resuspendability and injection.

In both single shipments and combined shipments, maintaining the same orientation of the syringes during initial storage and shipment leads to syringes that are more difficult to resuspend, resulting in more residual product after 5 seconds of rapid resuspendability and manual injection.

Tables 9-11 provide the results for sets of samples and permit head to head comparison between syringes for which orientation between initial storage varied from that during shipment, as compared with syringes that remained in the same orientation during pre-shipping storage and shipment.

Experiments 1 and 2 represent two data sets from testing that involved a single type of simulated shipping, while Experiment 3 provides data from the combined shipping test (i.e., simulated air shipment followed by a simulated truck shipment).

TABLE 9

Experiment 1: Advantage of changes in orientation between pre shipping storage and shipping

| | Batch | Initial storage orientation | Shipping orientation | Shipping type | Storage position | Results after 5" rapid shaking | | | | | | | |
|---|---|---|---|---|---|---|---|---|---|---|---|---|---|
| | | | | | | 1 day Residue (mm) | Injection forces (N) | 3 weeks Residue (mm) | Injection forces (N) | 2 months Residue (mm) | Injection forces (N) | 3 months Residue (mm) | Injection forces (N) |
| | JHBOE | Horizontal | Horizontal | Air 1 h low level | Horizontal | 1 | 43 | 8 | 55 | 4 | 53 | 2 | 48 |
| | JHBOE | Horizontal | Horizontal | Air 1 h low level | Horizontal | | | | | 4 | 57 | 4 | 53 |
| Average | JHBOE | Horizontal | Horizontal | Air 1 h low level | Horizontal | 1 | 43 | 8 | 55 | 4 | 55 | 3 | 51 |
| | JHB53 | Tip Up | Horizontal | Air 1 h low level | Horizontal | 0 | 26 | 0 | 41 | 0 | 38 | 0 | 50 |
| | JHB53 | Tip Up | Horizontal | Air 1 h low level | Horizontal | | | | | 0 | 35 | 0 | 30 |
| Average | JHB53 | Tip Up | Horizontal | Air 1 h low level | Horizontal | 0 | 26 | 0 | 55 | 0 | 37 | 0 | 40 |
| Benefit | | | | | | 100% | 40% | 100% | 0% | 100% | 33% | 108% | 22% |

TABLE 10

Experiment 2: Advantage of change in orientation between pre-shipping storage and shipping.
Change in orientation between shipping and long term storage lesser effect

|  | Batch | Initial storage orientation | Shipping orientation | Shipping type | Storage position | 1 day Residue (mm) | Injection forces (N) | 3 weeks Residue (mm) | Injection forces (N) | 2 months Residue (mm) | Injection forces (N) | 3 months Residue (mm) | Injection forces (N) |
|---|---|---|---|---|---|---|---|---|---|---|---|---|---|
|  | JHBOE | Tip Up | Horizontal | Air 4 h high level | Horizontal | 0 | 21 | 0 | 50 | 0 | 40 | 0 | 35 |
|  | JHBOE | Tip Up | Horizontal | Air 4 h high level | Horizontal |  |  |  |  | 0 | 35 | 0 | 48 |
|  | JHB10 | Tip Up | Horizontal | Air 4 h high level | Horizontal | 0 | 22 | 0 | 41 | 0 | 33 | 3 | 52 |
|  | JHB10 | Tip Up | Horizontal | Air 4 h high level | Horizontal |  |  |  |  | 0 | 31 | 0 | 28 |
| Average | JHB10 | Tip Up | Horizontal | Air 4 h high level | Horizontal | 0 | 22 | 0 | 46 | 0 | 35 | 1 | 41 |
|  | JHBOE | Tip Up | Horizontal | Air 4 h high level | Tip Down | 0 | 26 | 0 | 30 | 0 | 30 | 0 | 32 |
|  | JHBOE | Tip Up | Horizontal | Air 4 h high level | Tip Down |  |  |  |  | 0 | 33 | 0 | 34 |
|  | JHB10 | Tip Up | Horizontal | Air 4 h high level | Tip Down | 0 | 24 | 0 | 23 | 0 | 33 | 0 | 32 |
|  | JHB10 | Tip Up | Horizontal | Air 4 h high level | Tip Down |  |  |  |  | 0 | 32 | 0 | 33 |
| Average | JHB10 | Tip Up | Horizontal | Air 4 h high level | Tip Down | 0 | 25 | 0 | 27 | 0 | 32 | 0 | 33 |
| Average |  | Tip Up | Horizontal | Air 4 h high level | Hot/ Tip Down | 0 | 23 | 0 | 36 | 0 | 33 | 0 | 37 |
|  | JEB5F | Tip Down | Tip Down | Air 4 h high level | Horizontal | 1 | 47 | 1 | 52 | 1 | 48 | 0 | 46 |
|  | JEB5F | Tip Down | Tip Down | Air 4 h high level | Horizontal |  |  |  |  | 2 | 50 | 0 | 49 |
|  | JEB5F | Tip Down | Tip Down | Air 4 h high level | Horizontal | 1 | 45 | 2 | 52 | 1 | 46 | 0 | 48 |
|  | JEB5F | Tip Down | Tip Down | Air 4 h high level | Horizontal |  |  |  |  | 0 | 43 | 1 | 57 |
| Average | JEB5F | Tip Down | Tip Down | Air 4 h high level | Horizontal | 1 | 46 | 2 | 52 | 1 | 46 | 0 | 48 |
|  | JEB5F | Tip Down | Tip Down | Air 4 h high level | Tip Down | 2 | 45 | 5 | 56 | 2 | 51 | 3 | 50 |
|  | JEB5F | Tip Down | Tip Down | Air 4 h high level | Tip Down |  |  |  |  | 3 | 49 | 4 | 54 |
|  | JEB5F | Tip Down | Tip Down | Air 4 h high level | Tip Down | 1 | 55 | 4 | 50 | 2 | 53 | 7 | 55 |
|  | JEB5F | Tip Down | Tip Down | Air 4 h high level | Tip Down |  |  |  |  | 3 | 56 | 5 | 53 |
| Average | JEB5F | Tip Down | Tip Down | Air 4 h high level | Tip Down | 1 | 50 | 5 | 53 | 3 | 52 | 5 | 53 |
| Average |  | Tip Down | Tip Down | Air 4 h high level | Hot/ Tip Down | 1 | 48 | 3 | 53 | 2 | 49 | 3 | 51 |
| Benefit |  |  |  |  |  | 100% | 52% | 100% | 31% | 100% | 32% | 85% | 27% |

TABLE 11

Experiment 3: Advantage of change orientation between pre shipping storage and shipping

| Batch | Initial storage orientation | Shipping orientation 1 | Shipping type 1 | Shipping orientation 2 | Shipping type 2 | Storage position | 1 day Residue (mm) | Injection forces (N) | 3 weeks Residue (mm) | Injection forces (N) | 2 months Residue (mm) | Injection forces (N) |
|---|---|---|---|---|---|---|---|---|---|---|---|---|
| JHB53 | Horizontal | Horizontal | Air 2 h medium level | Horizontal | Truck 4 h high | Horizontal | 5 | 55 | 6 | 57 | 4 | 51 |
| JHB53 | Horizontal | Horizontal | Air 2 h medium level | Horizontal | Truck 4 h high | Horizontal |  |  | 4 | 66 | 6 | 56 |

TABLE 11-continued

Experiment 3: Advantage of change orientation between pre shipping storage and shipping

| | | | | | | | | Results after 5" rapid shaking | | | | | |
|---|---|---|---|---|---|---|---|---|---|---|---|---|---|
| Batch | Initial storage orientation | Shipping orientation 1 | Shipping type 1 | Shipping orientation 2 | Shipping type 2 | Storage position | 1 day Residue (mm) | Injection forces (N) | 3 weeks Residue (mm) | Injection forces (N) | 2 months Residue (mm) | Injection forces (N) |
| JHB53 | Horizontal | Horizontal | Air 2 h medium level | Horizontal | Truck 4 h high | Horizontal | 5 | 55 | 5 | 62 | 5 | 54 |
| JHB53 | Tip Down | Horizontal | Air 2 h medium level | Horizontal | Truck 4 h high | Horizontal | 2 | 42 | 0 | 36 | 4 | 54 |
| JHB53 | Tip Down | Horizontal | Air 2 h medium level | Horizontal | Truck 4 h high | Horizontal | | | 0 | 37 | 0 | 47 |
| JHB53 | Tip Down | Horizontal | Air 2 h medium level | Horizontal | Truck 4 h high | Horizontal | 2 | 42 | 0 | 37 | 2 | 51 |
| Benefit | | | | | | | 60% | 24% | 100% | 41% | 60% | 6% |

These data demonstrated that syringes shipped in an orientation that varied from the orientation during storage prior to shipment were easier to resuspend than syringes that were maintained in an orientation during shipping that did not vary from the pre-shipping storage orientation.

What is claimed:

1. A method for improving resuspendability of a six-month paliperidone palmitate extended-release injectable suspension (PP6M) within a syringe that was in a tip-down orientation during pre-shipping storage, comprising shipping the syringe in a substantially horizontal orientation and maintaining the syringe in the substantially horizontal orientation during shipping, wherein the syringe is shipped by airplane, truck, boat, or railroad, or combinations thereof.

2. The method according to claim 1, further comprising monitoring the syringe during shipping to confirm maintenance of the substantially horizontal orientation.

3. The method according to claim 1, further comprising housing the syringe within a container comprising an outer surface that bears instructions for maintaining the container during shipping in the substantially horizontal orientation, that bears markings that indicate an orientation of the container that corresponds to maintaining the substantially horizontal orientation, or both.

4. The method according to claim 1, further comprising, subsequent to the shipping, maintaining the syringe at a storage location in the substantially horizontal orientation.

5. The method according to claim 1, wherein the syringe has a capacity of 5 mL, and includes a 20 gauge needle that is 1.5 inches long.

6. The method according to claim 1, wherein the PP6M contains about 1092 or 1560 mg of paliperidone palmitate.

7. The method according to claim 1, further comprising administering the PP6M from the syringe to a patient.

8. A method of treating schizophrenia comprising administering to a patient in need thereof a six-month paliperidone palmitate extended-release injectable suspension (PP6M) from a syringe, wherein the syringe has undergone pre-shipping storage in a tip-down orientation and has been shipped in a substantially horizontal orientation and in the substantially horizontal orientation during the shipping, and wherein the syringe was shipped by airplane, truck, boat, or railroad, or combinations thereof.

9. The method according to claim 8, wherein the PP6M contains about 1092 or 1560 mg of paliperidone palmitate.

10. The method according to claim 9, wherein the PP6M comprises about 280 mg/mL to about 350 mg/mL of paliperidone palmitate.

11. The method according to claim 9, wherein the PP6M comprises about 312 mg/mL of paliperidone palmitate.

12. The method according to claim 9, wherein the PP6M comprises:
about 280 mg/mL to about 350 mg/mL of paliperidone palmitate;
about 8 mg/mL to about 12 mg/mL of a wetting agent;
one or more buffering agents;
about 65 mg/mL to about 85 mg/mL of a suspending agent; and
water q.s. ad 100%.

13. The method according to claim 12, wherein the PP6M comprises:
about 312 mg/mL of paliperidone palmitate;
about 10 mg/mL of polysorbate 20 as a wetting agent; and
about 75 mg/mL of polyethylene glycol 4000 as a suspending agent.

14. The method according to claim 13, wherein the PP6M is from about pH 6.0 to about pH 8.0.

15. The method according to claim 14, wherein the one or more buffering agents comprise citric acid monohydrate, sodium dihydrogen phosphate monohydrate, disodium hydrogen phosphate anhydrous, or sodium hydroxide.

16. The method according to claim 15, wherein the syringe has a capacity of 5 mL, and includes a 20 gauge needle that is 1.5 inches long.

17. The method according to claim 6, wherein PP6M comprises about 280 mg/mL to about 350 mg/mL of paliperidone palmitate.

18. The method according to claim 6, wherein the PP6M comprises about 312 mg/mL of paliperidone palmitate.

19. The method according to claim 6, wherein the PP6M comprises:
about 280 mg/mL to about 350 mg/mL of paliperidone palmitate;
about 8 mg/mL to about 12 mg/mL of a wetting agent;
one or more buffering agents;
about 65 mg/mL to about 85 mg/mL of a suspending agent; and
water q.s. ad 100%.

20. The method according to claim 19, wherein the PP6M comprises:
  about 312 mg/mL of paliperidone palmitate;
  about 10 mg/mL of polysorbate 20 as a wetting agent; and
  about 75 mg/mL of polyethylene glycol 4000 as a suspending agent.

21. The method according to claim 20, wherein the PP6M is from about pH 6.0 to about pH 8.0.

22. The method according to claim 21, wherein the one or more buffering agents comprise citric acid monohydrate, sodium dihydrogen phosphate monohydrate, disodium hydrogen phosphate anhydrous, or sodium hydroxide.

23. The method according to claim 22, wherein the syringe has a capacity of 5 mL, and includes a 20 gauge needle that is 1.5 inches long.

24. The method according to claim 11, wherein the syringe has a capacity of 5 mL, and includes a 20 gauge needle that is 1.5 inches long.

25. The method according to claim 18, wherein the syringe has a capacity of 5 mL, and includes a 20 gauge needle that is 1.5 inches long.

\* \* \* \* \*

UNITED STATES PATENT AND TRADEMARK OFFICE
CERTIFICATE OF CORRECTION

PATENT NO. : 11,666,697 B2
APPLICATION NO. : 17/534837
DATED : June 6, 2023
INVENTOR(S) : Peter D'Hoore et al.

Page 1 of 1

It is certified that error appears in the above-identified patent and that said Letters Patent is hereby corrected as shown below:

In the Claims

Under Column no. 33, Claim 8, Line no. 64, Replace:
"and in"
With:
--and maintained in--

Under Column no. 34, Claim 17, Line no. 54, Replace:
"wherein PP6M"
With:
--wherein the PP6M--

Under Column no. 34, Claim 18, Line no. 57, Replace:
"wherein PP6M"
With:
--wherein the PP6M--

Signed and Sealed this
Twenty-ninth Day of April, 2025

Coke Morgan Stewart
*Acting Director of the United States Patent and Trademark Office*